(12) United States Patent
Desconclois et al.

(10) Patent No.: US 6,566,362 B2
(45) Date of Patent: May 20, 2003

(54) BENZO[F]NAPHTHYRIDINE DERIVATIVES, THEIR PREPARATION AND COMPOSITIONS CONTAINING THEM

(75) Inventors: Jean-François Desconclois, Paris (FR); Arielle Genevois-Borella, Thiais (FR); Philippe Girard, Ollainville (FR); Michel Kryvenko, Paris (FR); Marc Pierre Lavergne, Mandres les Roses (FR); Jean-Luc Malleron, Marcoussis (FR); Guy Picaut, Villejuif (FR); Michel Tabart, La Norville (FR); Sylvie Wentzler, Fresnes (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 10/029,950

(22) Filed: Dec. 31, 2001

(65) Prior Publication Data

US 2002/0137741 A1 Sep. 26, 2002

Related U.S. Application Data

(63) Continuation of application No. PCT/FR00/01819, filed on Jun. 29, 2000.
(60) Provisional application No. 60/148,212, filed on Aug. 12, 1999.

(30) Foreign Application Priority Data

Jun. 30, 1999 (FR) .............................. 99 08376

(51) Int. Cl.⁷ .................. A61K 31/4375; A61K 31/496; C07D 471/04; C07D 215/38; A61P 31/04
(52) U.S. Cl. ............. 514/253.03; 514/292; 514/211.15; 514/217.07; 514/252.04; 514/228.2; 514/226.8; 514/232.8; 514/256; 514/218; 540/544; 540/597; 540/575; 540/553; 544/55; 544/60; 544/96; 544/126; 544/361; 546/81; 546/88
(58) Field of Search ..................... 546/81, 88; 540/544, 540/597; 544/361, 55, 60, 96, 126; 524/292, 218, 253.03, 211.5, 217.07, 252.04, 228.2, 226.8, 232.8

(56) References Cited

U.S. PATENT DOCUMENTS 3,300,499 A 1/1967 Lesher

FOREIGN PATENT DOCUMENTS

| EP | 0 431 991 | 6/1991 |
|----|-----------|--------|
| FR | 2 258 855 | 8/1975 |
| GB | 1 492 029 | 11/1977 |

*Primary Examiner*—Evelyn Mei Huang
(74) *Attorney, Agent, or Firm*—Finnegan, Henderson, Farabow, Garrett & Dunner, L.L.P.

(57) ABSTRACT

Benzo[f]naphthyridine derivatives of formula (I):

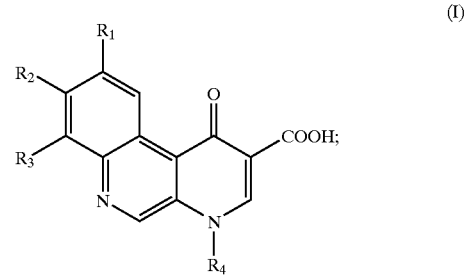

benzo[f]naphthyridine derivatives and benzo[f] naphthyridine esters of formula (IVa):

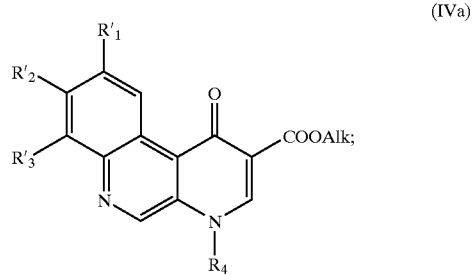

aminoquinoline derivatives of formula (X):

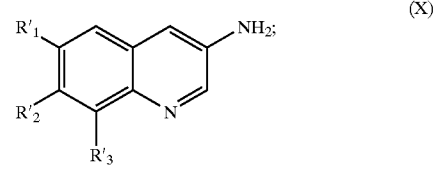

processes for preparing such compounds; and compositions comprising them.

12 Claims, No Drawings

BENZO[F]NAPHTHYRIDINE DERIVATIVES, THEIR PREPARATION AND COMPOSITIONS CONTAINING THEM

This application is a continuation application under 35 U.S.C. §111 (a) of International patent application no. PCT/FR00/01819, filed Jun. 29, 2000, and claims priority under 35 U.S.C. §119 to French patent application no. 99/08376, filed Jun. 30, 1999, and U.S. provisional patent application No. 60/148,212, filed Aug. 12, 1999.

The present invention relates to benzo[f]naphthyridine derivatives of formula (I):

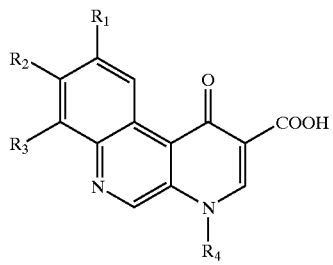

(I)

salts thereof, processes for preparing such compounds, and compositions comprising them.

European patent application no. EP 431 991 discloses benzo[b]naphthyridine derivatives of formula:

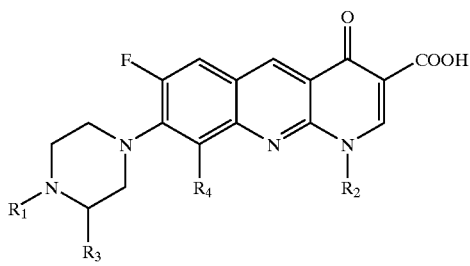

in which $R_1$ is H, hydroxyl or alkyl, $R_2$ is H, alkyl, fluoroalkyl, cycloalkyl, alkyloxy or alkylamino, $R_3$ is optionally substituted phenyl or phenylalkyl, and $R_4$ is H or a fluorine atom. These compounds are useful as antimicrobial agents.

French patent application no. FR 2 258 855 describes benzo[h]naphthyridine derivatives of formula:

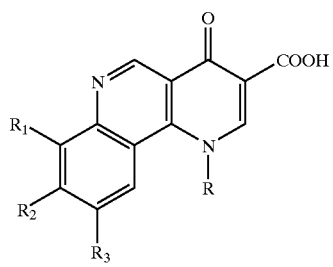

in which R is an alkyl radical, and $R_1$, $R_2$ and $R_3$, which are identical or different, are chosen from H, alkyl, polyhaloalkyl, halogen, alkoxy, nitro, alkylsulphone, sulphamide, or $R_1$ and $R_2$ or $R_2$ and $R_3$ may be linked to each other to constitute a novel saturated or unsaturated carbon-containing ring comprising 5 or 6 carbon atoms, it being possible for the bonding between these radicals themselves and the base nucleus to take place via one or two heteroatoms of oxygen to form a novel heterocycle. These compounds are useful as antimicrobial agents.

U.S. Pat. No. 3,300,499 describes benzo[f]naphthyridine derivatives of formula:

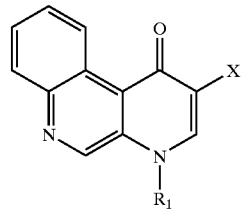

in which X is a carboxyl or alkyloxycarbonyl group, $R_1$ is an alkyl or alkenyl group, and the 5, 7, 8, 9 and 10 positions may also carry substituents chosen from alkyl, alkyloxy, hydroxyl, halogen, alkylamino and alkylthio.

However, these compounds have not been found to be active in tests for bacteriological activity in vitro carried out by the instant inventors.

The inventors have now found that benzo[f]naphthyridine derivatives of formula (I), salts thereof, and, where appropriate, stereoisomers thereof or mixtures of stereoisomers thereof:

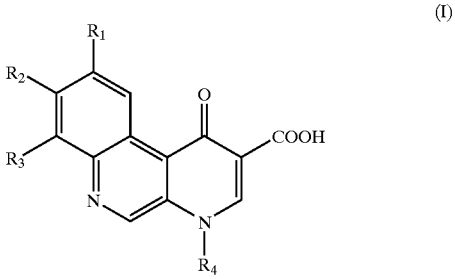

(I)

wherein:
$R_1$, $R_2$, and $R_3$, which are identical or different, may each be chosen from a hydrogen atom, halogen atoms, and groups of formula (II):

(II)

wherein:
$R_5$ and $R_6$ form, together with the nitrogen atom to which they are attached, a 5-, 6-, or 7-membered heterocycle, wherein 2 carbon atoms may optionally be linked to each other by a bridge containing 1 or 2 carbon atoms, wherein the heterocycle optionally comprises, in addition to the nitrogen atom, a heteroatom chosen from nitrogen, oxygen, and sulphur, and wherein the heterocycle may be optionally substituted with at least one group chosen from (i) an unsubstituted phenyl group, (ii) a phenyl group substituted with at least one group chosen from halogen atoms, alkyl groups, haloalkyl groups, alkyloxy groups, and a benzyloxy group, (iii) a benzyl group, (iv) alkyl groups, (v) a hydroxyl group, (vi) aminoalkyl groups, (vii) alkylaminoalkyl groups, (viii) dialkylaminoalkyl groups, and (ix) benzylaminoalkyl groups, provided that at least one of groups $R_1$, $R_2$, and $R_3$ is a group of formula (II), and provided that at least one of groups $R_1$, $R_2$, and $R_3$ is chosen from halogen atoms, $R_4$ is chosen from alkyl groups, fluoroalkyl groups, carboxyalkyl groups, ($C_3$ to $C_6$) cycloalkyl groups, a fluorophenyl group, a difluorophenyl group, alkyloxy groups, and alkylamino groups, and wherein the alkyl groups may be chosen from unbranched ($C_1$ to $C_4$) alkyl groups and branched ($C_1$ to $C_4$) alkyl groups, manifest advantageous antibacterial activity, for example, for the topical route.

In formula (I), the halogen substituents may be chosen from a chlorine atom, a fluorine atom, a bromine atom, and an iodine atom. Moreover, when $R_5$ and $R_6$ form, together with the nitrogen atom to which they are attached, a 5- to 7-membered heterocycle, the heterocycle may be chosen, with no limitation being implied, from pyrrolidine, imidazolidine, pyrazolidine, piperidine, piperazine, morpholine, thiomorpholine, thiazolidine, perhydroazepine, and perhydrodiazepine. In addition, the above-mentioned alkyl groups can be chosen from a methyl group, an ethyl group, a propyl group, an isopropyl group, an n-butyl group, a sec-butyl group, and a tert-butyl group.

According to one embodiment of the present invention, the benzo[f]naphthyridine derivatives can be chosen from derivatives of formula (I), salts thereof, and, where appropriate, stereoisomers thereof or mixtures of stereoisomers thereof:

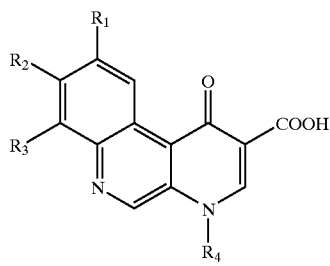

wherein:

$R_1$, $R_2$, and $R_3$, which are identical or different, may each be chosen from a hydrogen atom, halogen atoms, and groups of formula (II):

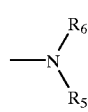

wherein:

$R_5$ and $R_6$ form, together with the nitrogen atom to which they are attached, a 6- or 7-membered heterocycle, wherein 2 carbon atoms may optionally be linked to each other by a bridge containing 1 or 2 carbon atoms, wherein the heterocycle optionally comprises an additional nitrogen atom, and wherein the heterocycle may be optionally substituted with at least one group chosen from (i) an unsubstituted phenyl group, (ii) a phenyl group substituted with at least one group chosen from halogen atoms, alkyl groups, haloalkyl groups, alkyloxy groups, and a benzyloxy group, and (iii) alkyl groups, provided that at least one of groups $R_1$, $R_2$, and $R_3$ is a group of formula (II), and provided that at least one of groups $R_1$, $R_2$, and $R_3$ is chosen from halogen atoms, $R_4$ is chosen from alkyl groups and fluoroalkyl groups, and wherein the alkyl groups may be chosen from unbranched ($C_1$ to $C_4$) alkyl groups and branched ($C_1$ to $C_4$) alkyl groups.

According to the invention, compounds of formula (I) may be prepared, for example, by reacting an amine of formula (III):

wherein:

$R_5$ and $R_6$ form, together with the nitrogen atom to which they are attached, a 5-, 6-, or 7-membered heterocycle, wherein 2 carbon atoms may optionally be linked to each other by a bridge containing 1 or 2 carbon atoms, wherein the heterocycle optionally comprises, in addition to the nitrogen atom, a heteroatom chosen from nitrogen, oxygen, and sulphur, and wherein the heterocycle may be optionally substituted with at least one group chosen from an (i) unsubstituted phenyl group, (ii) a phenyl group substituted with at least one group chosen from halogen atoms, alkyl groups, haloalkyl groups, alkyloxy groups, and a benzyloxy group, (iii) a benzyl group, (iv) alkyl groups, (v) a hydroxyl group, (vi) aminoalkyl groups, (vii) alkylaminoalkyl groups, (viii) dialkylaminoalkyl groups, and (ix) benzylaminoalkyl groups, with a benzo[f]naphthyridine derivative of formula (IV):

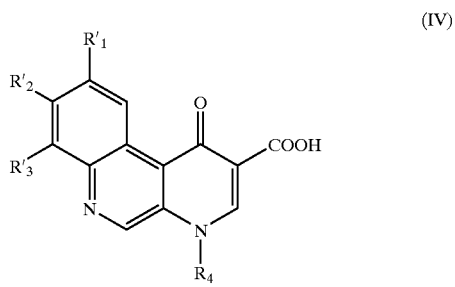

wherein:

$R_4$ is chosen from alkyl groups, fluoroalkyl groups, carboxyalkyl groups, ($C_3$ to $C_6$) cycloalkyl groups, a fluorophenyl group, a difluorophenyl group, alkyloxy groups, and alkylamino groups optionally comprising a protecting group, and $R'_1$, $R'_2$, and $R'_3$, which are identical or different, may each be chosen from a hydrogen atom and halogen atoms, provided that at least two of $R'_1$, $R'_2$, and $R'_3$ are chosen from halogen atoms, wherein the halogen atoms may be chosen from a fluorine atom, a chlorine atom, a bromine atom, and an iodine atom, separating the amine-containing compounds thus prepared, and optionally converting the separated compound formed above to a salt.

The reaction of amines of formula (III) can be performed in the presence of an excess of a derivative of formula (III), as an acid acceptor in suitable organic solvents. It is possible to carry out the procedure with or without solvent, at a temperature ranging, for example, from 20 to 150° C. When the procedure is carried out in the presence of a solvent, the reaction can be carried out in aprotic polar solvents, such as, for example, pyridine, dimethylformamide, dimethyl sulphoxide, and acetonitrile. It is also possible to carry out the procedure in an aqueous medium.

Such reactions may also be carried out in the presence of an acid acceptor such as, for example, a nitrogenous organic base (for example, triethylamine), an alkali metal carbonate (for example, sodium carbonate), or an alkali metal or alkaline-earth metal hydroxide.

When an amine of formula (III) is reacted with a benzo[f]naphthyridine derivative of formula (IV), a mixture of monoamine-containing compounds is obtained. These compounds may be separated by conventional separation techniques, for example by crystallization, or by preparative chromatography, such as, High-Performance Liquid Chromatography (HPLC) or medium-pressure chromatography ("flash chromatography"), so as to select a desired compound of formula (I).

Benzo[f]naphthyridine derivatives of formula (IV) may be prepared, for example, from a corresponding ester of formula (VI):

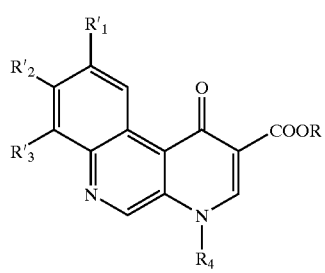

(VI)

wherein:

- $R'_1$, $R'_2$, and $R'_3$, which are identical or different, may each be chosen from a hydrogen atom and halogen atoms, provided that at least two of $R'_1$, $R'_2$, and $R'_3$ are chosen from halogen atoms,
- $R_4$ is chosen from alkyl groups, fluoroalkyl groups, carboxyalkyl groups, ($C_3$ to $C_6$) cycloalkyl groups, a fluorophenyl group, a difluorophenyl group, alkyloxy groups, and alkylamino groups optionally comprising a protecting group, and
- R is chosen from unbranched ($C_1$ to $C_4$) alkyl groups and branched ($C_1$ to $C_4$) alkyl groups, and
- wherein the halogen atoms are chosen from a fluorine atom, a chlorine atom, a bromine atom, and an iodine atom, by any known method for obtaining an acid from an ester without affecting the remainder of the molecule.

The preparation of an acid from an ester can generally be carried out by saponification in the presence of potassium hydroxide or of sodium hydroxide, in an aqueous or an aqueous-alcoholic medium, at a temperature ranging, for example, from 20 to 10° C. It is also possible to carry out the procedure by acid hydrolysis at temperatures as cited above.

Compounds of formulae (IV) and (VI), which may generically represented by formula (IVa):

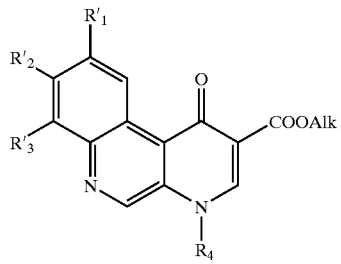

(IVa)

wherein:

- $R'_1$, $R'_2$, and $R'_3$, which are identical or different, may each be chosen from a hydrogen atom and halogen atoms, provided that at least two of $R'_1$, $R'_2$, and $R'_3$ are chosen from halogen atoms,
- Alk is chosen from a hydrogen atom, unbranched ($C_1$ to $C_4$) alkyl groups, and branched ($C_1$ to $C_4$) alkyl groups, and
- $R_4$ is chosen from alkyl groups, fluoroalkyl groups, carboxyalkyl groups, ($C_3$ to $C_6$) cycloalkyl groups, a fluorophenyl group, a difluorophenyl group, alkyloxy groups, and alkylamino groups optionally comprising a protecting group,
- wherein the halogen atoms are chosen from a fluorine atom, a chlorine atom, a bromine atom, and an iodine atom, are novel compounds, which are useful as intermediates for the synthesis of benzo[f]naphthyridines of formula (I) according to the present invention, and therefore constitute another subject of the present invention.

According to the invention, benzo[f]naphthyridine derivatives of formula (I) may also be prepared, for example, from a corresponding ester of formula (V):

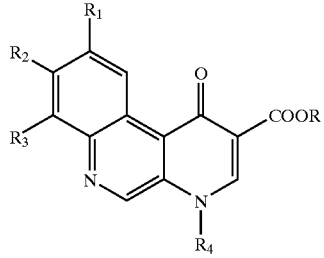

(V)

wherein:

- R is chosen from unbranched ($C_1$ to $C_4$) alkyl groups and branched ($C_1$ to $C_4$) alkyl groups,
- $R_1$, $R_2$, and $R_3$, which are identical or different, may each be chosen from a hydrogen atom, halogen atoms, and groups of formula (II):

(II)

wherein:

- $R_5$ and $R_6$ form, together with the nitrogen atom to which they are attached, a 5-, 6-, or 7-membered heterocycle, wherein 2 carbon atoms may optionally be linked to each other by a bridge containing 1 or 2 carbon atoms, wherein the heterocycle optionally comprises, in addition to the nitrogen atom, a heteroatom chosen from nitrogen, oxygen, and sulphur, and wherein the heterocycle may be optionally substituted with at least one group chosen from an (i) unsubstituted phenyl group, (ii) a phenyl group substituted with at least one group chosen from halogen atoms, alkyl groups, haloalkyl groups, alkyloxy groups, and a benzyloxy group, (iii) a benzyl group, (iv) alkyl groups, (v) a hydroxyl group, (vi) aminoalkyl groups, (vii) alkylaminoalkyl groups, (viii) dialkylaminoalkyl groups, and (ix) benzylaminoalkyl groups, provided that at least one of groups $R_1$, $R_2$, and $R_3$ is a group of formula (II), and provided that at least one of groups $R_1$, $R_2$, and $R_3$ is chosen from halogen atoms, and $R_4$ is chosen from alkyl groups, fluoroalkyl groups, carboxyalkyl groups, ($C_3$ to $C_6$) cycloalkyl groups, a fluorophenyl group, a difluorophenyl group, alkyloxy groups, and alkylamino groups optionally comprising a protecting group, by any known method for preparing an acid from an ester without affecting the remainder of the molecule, and optionally converting the acid formed above to a salt.

Preparation of acids from esters can generally be carried out by saponification in the presence of potassium hydroxide or of sodium hydroxide, in an aqueous or an aqueous-alcoholic medium, at a temperature ranging from, for example, 20 to 100° C. It is also possible to carry out the procedure by acid hydrolysis at temperatures as cited above.

When $R_4$ is chosen from alkylamino groups comprising a protecting group, the protecting group may be chosen from amino-protecting groups that are compatible with the molecule. In one embodiment, a protecting group that may be removed simultaneously with hydrolysis of the ester can be used. Protection of the alkylamino group may be carried out by any compatible group whose use and removal does not adversely affect the remainder of the molecule. For example, the procedure may be carried out according to the methods described by T. W. Greene, *Protective Groups in Organic Synthesis*, A. Wiley-Interscience Publication (1981), or the methods described by Mc OMIE, *Protective Groups in Organic Chemistry*, Plenum Press (1973).

Benzo[f]naphthyridine derivatives of formula (V) may be prepared, for example, by reacting an amine of formula (III) with a corresponding ester of formula (VI) as defined above, according to the same method as that described above for the reaction of an amine of formula (III) with a benzo[f] naphthyridine derivative of formula (IV), wherein a derivative of formula (I) is prepared. It is understood that where an amine of formula (III) is reacted with a benzo[f] naphthyridine derivative of formula (IV) in an aqueous medium, it is possible to directly prepare a compound of formula (I) without intermediate isolation of a derivative of formula (V).

Benzo[f]naphthyridine esters of formula (VI) may be prepared, for example, by:

a) reacting a malonate derivative of formula (IX):

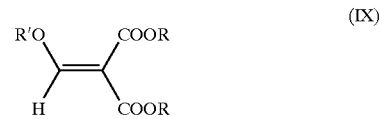

wherein:

R and R', which are identical or different, may each be chosen from unbranched ($C_1$ to $C_4$) alkyl groups and branched ($C_1$ to $C_4$) alkyl groups, with an aminoquinoline of formula (X):

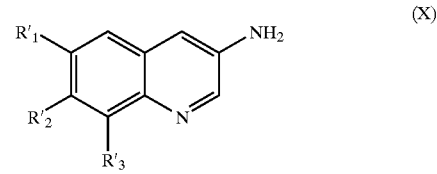

wherein:

$R'_1$, $R'_2$, and $R'_3$, which are identical or different, may each be chosen from a hydrogen atom and halogen atoms, provided that at least two of $R'_1$, $R'_2$, and $R'_3$ are chosen from halogen atoms, to form a derivative of formula (VIII):

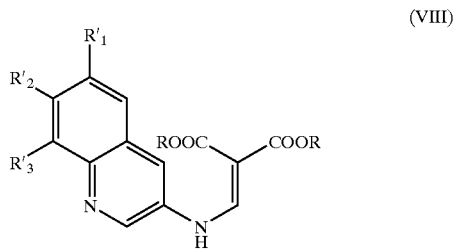

wherein:

$R'_1$, $R'_2$, and $R'_3$ are defined as above with respect to formula (X), and R is defined as above with respect for formula (IX), b) cyclizing the compound of formula (VIII), formed in (a) above, by thermal cyclization of the Gould-Jacob type, to form a compound of formula (VII):

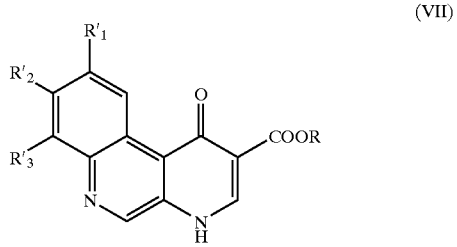

wherein:

$R'_1$, $R'_2$, and $R'_3$ are defined as above with respect to formula (X), and R is defined as above with respect for formula (IX), c) reacting the compound of formula (VII), formed in (b) above, with a halogenated derivative of formula R₄-Hal, wherein:

R₄ is chosen from alkyl groups, fluoroalkyl groups, carboxyalkyl groups, (C₃ to C₆) cycloalkyl groups, a fluorophenyl group, a difluorophenyl group, alkyloxy groups, and alkylamino groups optionally comprising a protecting group, and Hal is a halogen atom chosen from a chlorine atom, a bromine atom, and an iodine atom, to form a benzo[f]naphthyridine ester of formula (VI):

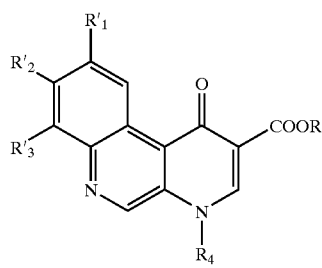

wherein:

R'₁, R'₂, and R'₃ are defined as above with respect to formula (X),

R₄ is defined as above with respect to formula (VII), and

R is defined as above with respect for formula (IX).

For the above-mentioned step a), the procedure can generally be carried out without solvent at a temperature ranging, for example, from 20 to 150° C., or in aromatic solvents, chlorinated solvents, or ethers at a temperature ranging, for example, from 20 to 110° C. Representative solvents that may be used include xylene, toluene, chloroform, methylene chloride, and diphenyl ether.

Thermal cyclization of the Gould-Jacob type can generally be carried out at a temperature ranging, for example, from 100 to 260° C. in diphenyl ether or in the eutectic ratio of the phenyl ether/biphenyl mixture (Angeles de la Cruz et al., Tetrahedron, 48(29), pp. 6135–6150, 1992).

The reaction according to step c) as described above can generally be carried out in a basic medium at a temperature ranging, for example, from 20 to 150° C., in an appropriate organic solvent. As compatible base, alkali metal or alkaline-earth metal carbonates, for example, potassium carbonate, sodium carbonate, and the like, may be used. In one embodiment, such a procedure can be carried out in a solvent chosen from dimethylformamide and dimethyl sulphoxide.

Aminoquinolines of formula (X), and salts thereof when they exist, are new compounds, which are useful as intermediates in the preparation of benzo[f]naphthyridine derivatives of formula (I) according to the present invention, and therefore also constitute another subject of the present invention. Aminoquinolines of formula (X) may be prepared, for example, in various ways. For example, aminoquinolines of formula (X) may be prepared, for example, by reducing a corresponding nitroquinoline of formula (XI):

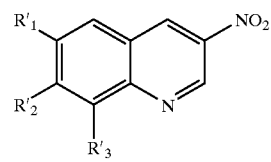

wherein:

R'₁, R'₂, and R'₃, which are identical or different, may each be chosen from a hydrogen atom and halogen atoms, provided that at least two of R'₁, R'₂, and R'₃ are chosen from halogen atoms.

Such a reduction can be carried out, for example, according to known, conventional methods which do not affect the halogenated substituents, for example, by catalytic hydrogenation in an acidic medium in the presence of Raney nickel or of palladium on carbon, in an alcohol and at a temperature ranging, for example, from 20 to 60° C. The alcohol may be chosen from, for example, methanol and ethanol.

Further, for example, aminoquinolines of formula (X) may be prepared, for example, by carrying out the procedure by the action of tin(II) chloride in an acidic aqueous medium, at a temperature ranging, for example, from 20 to 100° C., or by reduction with iron in an acidic aqueous and alcoholic medium at a temperature ranging, for example, from 20 to 100° C. The acidic aqueous medium may be, for example, an aqueous hydrochloric acid solution. The alcoholic solution may be, for example, chosen from methanol and ethanol.

Nitroquinolines of formula (XI) may be prepared, for example, by reacting methazonic acid with a benzaldehyde derivative of formula (XII):

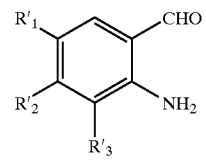

wherein:

R'₁, R'₂, and R'₃, which are identical or different, may each be chosen from a hydrogen atom and halogen atoms, provided that at least two of R'₁, R'₂, and R'₃ are chosen from halogen atoms.

Such a procedure can generally be carried out at a temperature ranging, for example, from 20 to 50° C., in an acidic aqueous medium which may be, for example, an aqueous hydrochloric acid solution.

Benzaldehyde derivatives of formula (XII) may be prepared, for example, by reacting a corresponding halogenated derivative of aniline of formula (XIII):

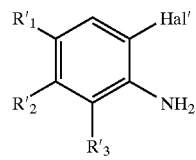

wherein:

R'₁, R'₂, and R'₃, which are identical or different, may each be chosen from a hydrogen atom and halogen atoms, provided that at least two of $R'_1$, $R'_2$, and $R'_3$ are chosen from halogen atoms, and Hal' is a halogen atom chosen from a chlorine atom, a bromine atom, and an iodine atom, with an organolithium compound in an ether at a temperature ranging, for example, from −75 to 20° C., and adding dimethylformamide. Butyllithium may be mentioned as an organolithium compound, with no limitation being implied. In one embodiment, the procedure can be carried out, for example, in tetrahydrofuran.

The compounds of formula (XIII) are commercially available or may be prepared, for example, by analogous preparation techniques used for halogenation of anilines, for example, by the action of a halosuccinimide in an aprotic polar solvent at a temperature ranging, for example, from −20 to 100° C. It is possible, for example, to carry out the procedure in dimethylformamide.

Aminoquinolines of formula (X) may also be prepared, for example, by Hoffmann degradation of an amide from a corresponding carboxamide derivative of formula (XIV):

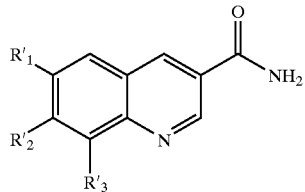

(XIV)

wherein:

$R'_1$, $R'_2$, and $R'_3$, which are identical or different, may each be chosen from a hydrogen atom and halogen atoms, provided that at least two of $R'_1$, $R'_2$, and $R'_3$ are chosen from halogen atoms.

The reaction can generally be carried out by the action of an oxidizing agent compatible with the reaction of Hoffmann degradation of an amide, at a temperature ranging, for example, from −20 to 100° C. As an oxidizing agent compatible with the reaction, it is possible to use, for example, sodium hypobromite, lead tetraacetate, or hypervalent derivatives of iodine such as, for example, 1,1-bis (trifluoroacetoxy)-iodobenzene and the like.

It is also possible to carry out the procedure according to any known method for preparing an amine from a carboxamide without affecting the remainder of the molecule.

Carboxamide derivatives of formula (XIV) may be prepared, for example, from a corresponding carboxyl derivative of formula (XV):

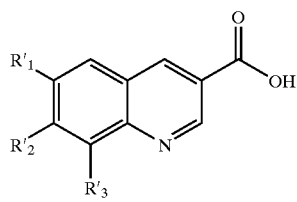

(XV)

wherein:

$R'_1$, $R'_2$, and $R'_3$, which are identical or different, may each be chosen from a hydrogen atom and halogen atoms, provided that at least two of $R'_1$, $R'_2$, and $R'_3$ are chosen from halogen atoms, according to known, art-recognized amidation methods for preparing a carboxamide from a corresponding acid without affecting the remainder of the molecule.

For example, such a procedure can be carried out by addition of thionyl chloride in a chlorinated solvent at a temperature ranging, for example, from 20 to 80° C., and then the acid chloride thus prepared can be treated with a stream of ammonia in methylene chloride at a temperature ranging, for example, from −10 to 20° C. Chloroform, dichloromethane, and the like may, for example, be mentioned as chlorinated solvents.

Derivatives of formula (XV) may be prepared, for example, from corresponding esters of formula (XVI):

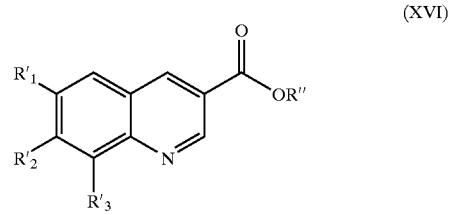

(XVI)

wherein:

$R'_1$, $R'_2$, and $R'_3$, which are identical or different, may each be chosen from a hydrogen atom and halogen atoms, provided that at least two of $R'_1$, $R'_2$, and $R'_3$ are chosen from halogen atoms, and R″ may be chosen from unbranched ($C_1$ to $C_4$) alkyl groups and branched ($C_1$ to $C_4$) alkyl groups, by any known method for preparing an acid from an ester without affecting the remainder of the molecule.

The preparation of the acid from the ester can generally be carried out according to the methods described above.

Ester derivatives of formula (XVI) may be prepared, for example, by catalytic hydrogenation in a basic medium, in the presence of palladium on carbon, of a halogenated derivative of formula (XVII):

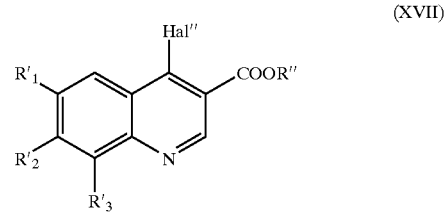

(XVII)

wherein:

$R'_1$, $R'_2$, and $R'_3$, which are identical or different, may each be chosen from a hydrogen atom and halogen atoms, provided that at least two of $R'_1$, $R'_2$, and $R'_3$ are chosen from halogen atoms, R″ may be chosen from unbranched ($C_1$ to $C_4$) alkyl groups and branched ($C_1$ to $C_4$) alkyl groups, and Hal″ is a halogen atom chosen from a chlorine atom, a bromine atom, and an iodine atom.

Such a procedure can generally be carried out in an alcohol, for example, methanol or ethanol, in the presence of a base, such as, triethylamine or diisopropylamine, and palladium on carbon at a temperature ranging, for example, from 20 to 60° C.

Derivatives of formula (XVII) may be prepared, for example, by halogenating a derivative of formula (XVIII):

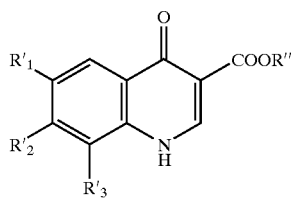

(XVIII)

wherein:

$R'_1$, $R'_2$, and $R'_3$, which are identical or different, may each be chosen from a hydrogen atom and halogen atoms, provided that at least two of $R'_1$, $R'_2$, and $R'_3$ are chosen from halogen atoms, and R" may be chosen from unbranched ($C_1$ to $C_4$) alkyl groups and branched ($C_1$ to $C_4$) alkyl groups.

Such a procedure can generally be carried out in the presence of phosphorus oxychloride or of phosphorus oxybromide, at a temperature ranging, for example, from 20 to 120° C.

Derivatives of formula (XVIII) may be prepared, for example, from a derivative of formula (XIX):

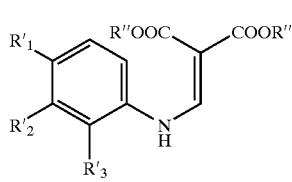

(XIX)

wherein:

$R'_1$, $R'_2$, and $R'_3$, which are identical or different, may each be chosen from a hydrogen atom and halogen atoms, provided that at least two of $R'_1$, $R'_2$, and $R'_3$ are chosen from halogen atoms, and R" may be chosen from unbranched ($C_1$ to $C_4$) alkyl groups and branched ($C_1$ to $C_4$) alkyl groups, according to the method described in Angeles de la Cruz et al., Tetrahedron, 48(29), pp. 6135–6150 (1992).

The procedure can also be carried out in a manner similar to the method described above for passing from a derivative of formula (VIII) to a derivative of formula (VII) (step b for the preparation of benzo[f]naphthyridine esters of formula (VI)), or by any other similar known, art-recognized method.

Derivatives of formula (XIX) may be prepared, for example, by reacting an aniline derivative of formula (XX):

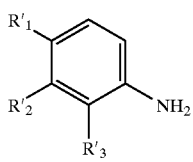

(XX)

wherein:

$R'_1$, $R'_2$, and $R'_3$, which are identical or different, may each be chosen from a hydrogen atom and halogen atoms, provided that at least two of $R'_1$, $R'_2$, and $R'_3$ are chosen from halogen atoms, with a malonate derivative of formula (XXI):

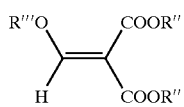

(XXI)

wherein:

R" and R'", which may be identical or different, may each be chosen from unbranched ($C_1$ to $C_4$) alkyl groups and branched ($C_1$ to $C_4$) alkyl groups, according to methods similar to that described by Angeles de la Cruz et al., Tetrahedron, 48(29), pp. 6135–6150 (1992).

Such a procedure can be carried out, for example, under operating conditions similar to those described above for passing from a derivative of formula (X) to a derivative of formula (VIII).

Aniline derivatives of formula (XX) are commercially available or may be prepared, for example, according to conventional methods, for example, by reducing a corresponding nitro derivative without affecting the halogenated substituents. Further, for example, a derivative of formula (XX) may be prepared, for example, according to conventional methods of halogenating anilines, such as is described above.

According to the invention, where appropriate, when stereoisomeric forms of the benzo[f]naphthyridine derivatives of formula (I) exist and when it is desired to obtain these stereoisomers, the separation of the stereoisomeric forms of the amines of formula (III) can be carried out by any known method compatible with the molecule. By way of example, the separation can be carried out by acylation by means of an acid or a reactive derivative of a chiral acid, separation of the isomers by high-performance liquid chromatography, and then deacylation according to the method described by P. G. Gasseman et al., J. Am. Chem. Soc., 98(5), p. 1275 (1976). It is also possible to carry out the separation of the stereoisomers by chiral phase high-performance liquid chromatography.

The new compounds according to the present invention as well as their synthetic intermediates may be optionally purified by conventional physical methods, such as crystallization or chromatography.

Compounds of formula (I) according to the present invention, as well as intermediates of formula (IV), may be converted to metal salts or to addition salts with nitrogenous bases according to known methods. These salts may be prepared, for example, according to known, art-recognized methods which do not adversely affect the remainder of the molecule, such as, for example, by reacting a metal base (for example, alkaline or alkaline-earth metal bases), ammonia or an amine with an above-mentioned compound in an appropriate solvent such as an alcohol, an ether or water, or by an exchange reaction with a salt of an organic acid. The salt formed precipitates after optional concentration of its solution, it is separated by filtration, decantation and/or lyophilization.

The new compounds according to the invention may also be converted to addition salts with acids. The compounds of formula (I) prepared in the form of these salts may be released and converted to salts of other acids according to known, art-recognized methods.

Representative pharmaceutically acceptable salts include, for example, salts with alkali metals (for example, sodium, potassium, and lithium), salts with alkaline-earth metals (for example, magnesium and calcium), ammonium salts, salts of nitrogenous bases (for example, ethanolamine, diethanolamine, trimethylamine, triethylamine, methylamine, propylamine, diisopropylamine, N,N-dimethylethanolamine, benzylamine, dicyclohexylamine, N-benzylphenethylamine, N,N'-dibenzylethylenediamine, diphenylenediamine, benzhydrylamine, quinine, choline, arginine, lysine, leucine, and dibenzylamine), as well as addition salts with inorganic acids (for example, hydrochlorides, hydrobromides, sulphates, nitrates, and phosphates), and addition salts with organic acids (for exmaple, succinates, fumarates, maleates, methanesulphonates, p-toluenesulphonates, and isethionates).

Benzo[f]naphthyridine derivatives of formula (I) according to the present invention and their pharmaceutically acceptable salts exhibit advantageous antibacterial properties. They manifest a remarkable activity in vitro and in vivo on Gram-positive microorganisms and for example on microorganisms resistant to quinolones. Taking into account their activity, they are appropriate, for example, for use by the topical route.

In vitro, compounds of formula (I) are active at a concentration ranging, for example, from 1 to 4 $\mu g/cm^3$, on *Staphylococcus aureus* IP 8203 and at a concentration ranging, for example, from 1 to 8 $\mu g/cm^3$, on *Staphylococcus aureus* LF11C128B, which are resistant to quinolones.

In vivo, the compounds are active at a concentration ranging, for example, from 2% to 5% in a cetomacrogol and benzyl alcohol formulation, in the model of infection of guinea-pigs with *Staphylococcus aureus* TCC25923.

Compounds according to the present invention do not exhibit toxicity at the doses used. The level of skin irritation measured in rabbits as a formulation in cetomacrogol and benzyl alcohol, is 1 for a formulation containing 1% of at least one compound according to the invention in the excipient, compared with 0.8 for the excipient alone. Furthermore, a formulation containing 10% of at least one compound according to the invention in the above excipient did not show greater irritation in guinea-pigs.

The following examples, given with no limitation being implied, illustrate the present invention.

EXAMPLE 1

8-chloro-7-fluoro-9-[4-(3-fluoro-4-methyl phenyl) piperazin-1-yl]-4-methyl-1-oxo-1,4-dihydrobenzo[f][1,7] naphthyridine-2-carboxylic Acid was Prepared According to the Following Method:

A stirred suspension of 0.61 g of ethyl 8-chloro-7-fluoro-9-[4-(3-fluoro-4-methylphenyl)piperazin-1-yl]-4-methyl-1-oxo-1,4-dihydrobenzo[f][1,7]naphthyridine-2-carboxylate in 15 cm³ of ethanol and 1.4 cm³ of 1 N aqueous potassium hydroxide was heated in the region of 100° C. for 11 hours. The solution obtained was acidified at this same temperature with 1.5 cm³ of a 1 N aqueous acetic acid solution.

After cooling, the insoluble material was dewatered and then washed twice with 5 cm³ of water, once with 5 cm³ of ethanol, and twice with 5 cm³ of diethyl ether. After recrystallization from 50 cm³ of dimethylformamide, 0.40 g of 8-chloro-7-fluoro-9-[4-(3-fluoro-4-methylphenyl)piperazin-1-yl]-4-methyl-1-oxo-1,4-dihydrobenzo[f][1,7] naphthyridine-2-carboxylic acid was obtained in the form of a yellow solid, which melted at 360° C.

Ethyl 8-chloro-7-fluoro-9-[4-(3-fluoro-4-methylphenyl) piperazin-1-yl]-4-methyl-1-oxo-1,4-dihydrobenzo[f][1,7] naphthyridine-2-carboxylate was Prepared in the Following Manner:

A stirred suspension of 1 g of ethyl 8-chloro-7,9-difluoro-4-methyl-1-oxo-1,4-dihydrobenzo[f][1,7]naphthyridine-2-carboxylate and 1.2 g of 1-(3-fluoro-4-methylphenyl) piperazine in 15 cm³ of dimethyl sulphoxide was heated to a temperature in the region of 80° C. After 20 hours, 0.6 g of 1-(3-fluoro-4-methylphenyl)piperazine was added and the heating was continued for an additional 8 hours. After 28 hours, the reaction mixture was cooled and then filtered. The precipitate was washed twice with 10 cm³ of water, twice with 5 cm³ of ethanol, and twice with 5 cm³ of diisopropyl ether. 0.64 g of ethyl 8-chloro-7-fluoro-9-[4-(3-fluoro-4-methylphenyl)piperazin-1-yl]-4-methyl-1-oxo-1,4-dihydrobenzo[f][1,7]naphthyridine-2-carboxylate was obtained in the form of a greenish-yellow solid, which melted at 350° C. with decomposition.

Ethyl 8-chloro-7,9-difluoro-4-methyl-1-oxo-1,4-dihydrobenzo[f][1,7]naphthyridine-2-carboxylate was Prepared in the Following Manner:

A stirred suspension of 5.2 g of ethyl 8-chloro-7,9-difluoro-1-oxo-1,4-dihydrobenzo[f][1,7]naphthyridine-2-carboxylate and 4.15 g of anhydrous potassium carbonate in 50 cm³ of dimethylformamide was heated at a temperature in the region of 110° C. for 1 hour. After cooling to the region of 50° C., 3.7 cm³ of iodomethane was added dropwise. The mixture was again heated at a temperature in the region of 100° C. for 2 hours.

The reaction mass was cooled and then dewatered. The precipitate was washed 3 times with 20 cm³ of water, twice with 15 cm³ of ethanol, and twice with 15 cm³ of diethyl ether. 4.7 g of ethyl 8-chloro-7,9-difluoro-4-methyl-1-oxo-1,4-dihydrobenzo[f][1,7]naphthyridine-2-carboxylate was obtained in the form of a beige solid, which melted at 293° C.

Ethyl 8-chloro-7,9-difluoro-1-oxo-1,4-dihydrobenzo[f] [1,7]naphthyridine-2-carboxylate was Prepared in the Following Manner:

A mixture of 6.7 g of diethyl 7-chloro-6,8-difluoro-3-quinolylamino-methylidinemalonate and 70 cm³ of diphenyl ether was heated at a temperature in the region of 240° C. for 30 minutes. The reaction mass was cooled, the precipitate was dewatered, and the precipitate was washed 5 times with 20 cm³ of diethyl ether. 5.3 g of ethyl 8-chloro-7,9-difluoro-1-oxo-1,4-dihydrobenzo[f][1,7]naphthyridine-2-carboxylate was obtained in the form of a beige solid, which melted at 328° C.

Diethyl 7-chloro-6,8-difluoro-3-quinolylaminomethylidinemalonate was Prepared in the Following Manner:

A mixture of 4.25 g of 3-amino-7-chloro-6,8-difluoroquinoline and 4.4 cm³ of diethyl ethoxymethylidinemalonate was heated at a temperature in the region of 120° C., with stirring, for 1 hour. The reaction was terminated by an additional heating for 15 minutes at a temperature in the region of 150° C.

The cooled reaction mass was taken up in 30 cm³ of diisopropyl ether, filtered, and washed twice with 15 cm³ of diisopropyl ether. 6.8 g of diethyl 7-chloro-6,8-difluoro-3-quinolylaminomethylidinemalonate was obtained in the form of a beige solid, which melted at 175° C.

3-Amino-7-chloro-6,8-difluoroquinoline was Prepared in the Following Manner:

4 g of 7-chloro-6,8-difluoro-3-nitroquinoline was reduced in 200 cm³ of ethanol, in the presence of about 1 g of Raney nickel, with hydrogen, at atmospheric pressure, and at a temperature in the region of 20° C. for 75 min.

After addition of 100 cm³ of dimethylformamide to the reaction mass, the catalyst was filtered off and the solution concentrated under reduced pressure (5 kPa) at a temperature in the region of 60° C. The residue was taken up in 20 cm³ of ethanol, dewatered, and washed twice with 15 cm³ of diethyl ether. 3 g of 3-amino-7-chloro-6,8-difluoroquinoline was obtained in the form of a yellow solid, which melted at 270° C.

7-Chloro-6,8-difluoro-3-nitroquinoline was Prepared in the Following Manner:

17.4 g of methazonic acid and 60 cm³ of a 37% aqueous hydrochloric acid solution were rapidly added, with stirring, to a solution of 8.7 g of 2-amino-4-chloro-3,5-difluorobenzaldehyde in 300 cm³ of ethanol, while the mixture was maintained at a temperature in the region of 35° C. The mixture was stirred for 16 hours at a temperature in the region of 20° C. The precipitate was dewatered and washed 3 times with 25 cm³ of diethyl ether. 8.1 g of 7-chloro-6,8-difluoro-3-nitroquinoline was obtained in the form of an orange-colored solid, which melted at 174° C.

2-Amino-4-chloro-3,5-difluorobenzaldehyde was Prepared in the Following Manner:

66 cm³ of a 2 N butyllithium solution (in hexane) was added dropwise over 30 minutes to a stirred solution of 13.4 g of 2-bromo-5-chloro-4,6-difluoroaniline in 150 cm³ of anhydrous tetrahydrofuran (THF) cooled to a temperature in the region of –75° C. After stirring for 1 hour at this temperature, 12.8 cm³ of dimethylformamide was added. After the addition, the mixture was again stirred for 3 hours at a temperature in the region of –70° C. The mixture was brought to a temperature in the region of –5° C., and then an aqueous ammonium chloride solution (18 g dissolved in 180 cm³) was added. The reaction mixture was extracted twice with 200 cm of diethyl ether. The combined ethereal extracts were washed once with 150 cm³ of water and once with 150 cm³ of a saturated aqueous sodium chloride solution. After drying over magnesium sulphate, the solution was concentrated under reduced pressure (5 kPa), at a temperature in the region of 40° C. After taking up the solid residue obtained in 80 cm³ of hexane and then filtration, 6.2 g of 2-amino-4-chloro-3,5-difluorobenzaldehyde was obtained in the form of a yellow solid.

2-Bromo-5-chloro-4,6-difluoroaniline was Prepared in the Following Manner:

18.9 g of N-bromosuccinimide was gradually added to a stirred solution of 17.4 g of 3-chloro-2,4-difluoroaniline in 150 cm³ of dry dimethylformamide, cooled to a temperature in the region of –20° C., while this temperature was maintained. After stirring for 1 hour, the temperature was brought to the region of 20° C. and then the mixture was concentrated under reduced pressure (5 kPa), at a temperature in the region of 60° C. The residue obtained was supplemented with 400 cm³ of hexane and 200 cm³ of water. The mixture was stirred and the aqueous phase decanted off. The latter was extracted three times with successively 200, 200, and 100 cm³ of hexane. The extracts were combined, washed twice with 200 cm³ of water and twice with 200 cm³ of a saturated aqueous sodium chloride solution. After drying over magnesium sulphate, the organic solution was concentrated under reduced pressure (5 kPa) at a temperature in the region of 40° C. 19.2 g of 2-bromo-5-chloro-4,6-difluoroaniline was obtained in the form of a white solid, which melted at 62° C.

3-Chloro-2,4-difluoroaniline was Prepared in the Following Manner:

135 g of tin(II) chloride (dihydrate) was added in small fractions to a stirred suspension of 23 g of 3-chloro-2,4-difluoronitrobenzene in 110 cm³ of a 37% aqueous hydrochloric acid solution and 25 cm³ of diethyl ether. After the addition, the mixture was heated for 30 minutes at a temperature in the region of 40° C. After cooling the reaction mass, the mixture was poured over 300 cm³ of water supplemented with 150 g of ice. The mixture was made highly alkaline by addition of caustic soda, and then extracted twice with 250 cm³ of chloroform. The extracts were combined, dried over magnesium sulphate, and then concentrated under reduced pressure (5 kPa) at a temperature in the region of 40° C. 17.4 g of 3-chloro-2,4-difluoroaniline was obtained in the form of a beige solid, which melted at 58° C.

EXAMPLE 2

8-Fluoro-4-methyl-1-oxo-9-(1,3,3-trimethyl-6-azabicyclo[3.2.1]oct-6-yl)-1,4-dihydrobenzo[f][1,7]napththyridine-2-carboxylic Acid was Prepared in the Following Manner:

A suspension of 0.72 g of ethyl 8-fluoro-4-methyl-1-oxo-9-(1,3,3-trimethyl-6-azabicyclo[3.2.1]oct-6-yl)-1,4-dihydrobenzo[f][1,7]napththyridine-2-carboxylate in a mixture of 60 cm³ of ethanol at 50% and 1.9 cm³ of a 1 N aqueous potassium hydroxide solution was heated, with stirring, for 3 hours at a temperature in the region of 70° C. After being concentrated under reduced pressure (5.2 kPa) at 60° C., the residue was dissolved in 75 cm³ of water. A very light insoluble material was removed by filtration; the solution obtained was neutralized with 1.9 cm³ of a 1 N aqueous hydrochloric acid solution. The insoluble material formed was dewatered, washed 3 times with 25 cm³ of water, and dried under vacuum at 100° C. 0.60 g of 8-fluoro-4-methyl-1-oxo-9-(1,3,3-trimethyl-6-azabicyclo[3.2.1]oct-6-yl)-1,4-dihydrobenzo[f][1,7]napththyridine-2-carboxylic acid was obtained in the form of a yellow solid, which melted at 200° C.

Ethyl 8-fluoro-4-methyl-1-oxo-9-(1,3,3-trimethyl-6-azabicyclo[3.2.1]oct-6-yl)-1,4-dihydrobenzo[f][1,7]naphthyridine-2-carboxylate was Prepared in the Following Manner:

A suspension of 2 g of ethyl 8,9-difluoro-4-methyl-1-oxo-1,4-dihydrobenzo[f][1,7]naphthyridine-2-carboxylate and 2.6 g of 1,3,3-trimethyl-6-azabicyclo[3.2.1]octane in 50 cm³ of dimethyl sulphoxide was heated, with stirring, at a temperature of 90° C. for 12 days. After cooling to 20° C., the mixture was poured into 200 cm³ of ice-cold water. The medium was extracted 3 times with 200 cm³ of dichloromethane, and the organic extracts were washed 3 times with 100 cm³ of water, and dried over sodium sulphate. After filtration and concentration under reduced pressure (5.2 kPa), the compound obtained was purified by chromatography on 160 g of silica gel (0.06–0.20 mm). Elution was carried out with 3 liters of a dichloromethane-ethanol mixture (97-3 by volume), collecting 200 cm³ fractions. The fractions between 1.65 and 3 liters were concentrated to dryness under reduced pressure (5.2 kPa). 0.9 g of ethyl 8-fluoro-4-methyl-1-oxo-9-(1,3,3-trimethyl-6-azabicyclo[3.2.1]oct-6-yl)-1,4-dihydrobenzo[f][1,7]naphthyridine-2-carboxylate was obtained in the form of yellow crystals, which melted at 187° C.

Ethyl 8,9-difluoro-4-methyl-1-oxo-1,4-dihydrobenzo[f][1,7]naphthyridine-2-carboxylate was Prepared in the Following Manner:

A suspension of 28.8 g of ethyl 8,9-difluoro-4-oxo-1,4-dihydrobenzo[f][1,7]naphthyridine-2-carboxylate and 39 g of potassium carbonate in 450 cm³ of dimethyl sulphoxide was heated, with stirring, at a temperature of 90° C. for 3 hours. After cooling to about 50° C., 27 g of methyl iodide was added in portions. The mixture was heated at 65° C. for 3 hours; after cooling to 20° C., 250 cm³ of water and 200 g of ice were added to the reaction mixture. The insoluble material was dewatered, washed 3 times with 150 cm³ of water, and dissolved in 2 liters of dichloromethane. The residual water was decanted off; the organic extracts were dried over sodium sulphate in the presence of animal charcoal. After filtration and concentration under reduced pressure (5.2 kPa), the compound obtained was purified by chromatography on silica gel (0.06–0.20 mm). Elution was carried out with 6 liters of a dichloromethane-ethanol mixture (97-3 by volume), collecting 250 cm³ fractions. The fractions between 2 and 6 liters were concentrated to dryness under reduced pressure (5.2 kPa). 14 g of ethyl 8,9-difluoro-4-methyl-1-oxo-1,4-dihydrobenzo[f][1,7]naphthyridine-2-carboxylate was obtained in the form of white crystals, which melted at 272° C.

Ethyl 8,9-difluoro-1-oxo-1,4-dihydrobenzo[f][1,7]naphthyridine-2-carboxylate was Prepared in the Following Manner:

A suspension of 35.8 g of diethyl 6,7-difluoro-3-quinolylaminomethylidine-malonate in 250 cm³ of diphenyl ether was heated, with stirring, at a temperature of 230° C. for 1 hour. The ethanol formed was distilled off under an argon stream. After cooling to 50° C., 500 cm³ of hexane was added and the medium was cooled to 10° C. The precipitate obtained was dewatered and washed 3 times with 250 cm³ of diethyl ether. 29 g of ethyl 8,9-difluoro-1-oxo-1,4-dihydrobenzo[f][1,7]naphthyridine-2-carboxylate was obtained in the form of violet crystals, which melted at 300° C.

Diethyl 6,7-difluoro-3-quinolylaminomethylidinemalonate was Prepared in the Following Manner:

25 g of diethyl ethoxymethylidinemalonate was added to a suspension of 19.2 g of 3-amino-6,7-difluoroquinoline in 100 cm³ of toluene. The medium was heated, with stirring, at a temperature of 110° C. for 10 hours. It was concentrated to dryness under reduced pressure (5.5 kPa); the compound isolated was taken up, with stirring, in 200 cm³ of diisopropyl ether, dewatered, and washed twice with 100 cm³ of the same solvent. 35.9 g of diethyl 6,7-difluoro-3-quinolylaminomethylidinemalonate was obtained in the form of white crystals, which melted at 150° C.

3-Amino-6,7-difluoroquinoline was Prepared in the Following Manner:

33.2 g of 6,7-difluoroquinoline-3-carboxamide was added in portions, with stirring, to an aqueous sodium hypobromite solution at 0° C. The aqueous sodium hypobromite solution was obtained, with stirring, by slow addition of 28.5 g of bromine in 500 cm³ of a 2 N aqueous sodium hydroxide solution. The green solution obtained was stirred for 3 hours at 0° C. and heated for 3 hours at 60° C.

The brown suspension obtained was cooled to 0° C. and acidified with 70 cm³ of a 12 N aqueous hydrochloric acid solution. The insoluble material was extracted twice with 200 cm³ of diethyl ether, and the acidic aqueous extracts were neutralized with a 33% aqueous ammonium hydroxide solution. The insoluble material was dewatered, washed 3 times with 150 cm³ of water, and dissolved in 800 cm³ of diethyl ether. The organic extracts were washed 3 times with 100 cm³ of water, dried over sodium sulphate in the presence of 3 g of animal charcoal, filtered, and concentrated under reduced pressure (5.2 kPa). 20 g of 3-amino-6,7-difluoroquinoline was thus obtained in the form of white crystals, which melted at 155° C.

6,7-Difluoroquinoline-3-carboxamide was Prepared in the Following Manner:

58 g of thionyl chloride and 3 drops of dimethylformamide were added to a suspension of 34 g of 6,7-difluoroquinoline-3-carboxylic acid in 350 cm³ of chloroform. The mixture was heated, with stirring, at a temperature of 70° C. for 4 hours and concentrated under reduced pressure (5.2 kPa). The white compound obtained was suspended in 700 cm³ of dichloromethane at a temperature of −10° C.; a stream of ammonia was bubbled through, with vigorous stirring, while this temperature was maintained. The temperature of the mixture was allowed to rise to 20° C. over 1 hour, and the mixture was concentrated to dryness under reduced pressure (5.2 kPa), at a temperature of 50° C. The white residue, suspended with stirring in 800 cm³ of water for 15 minutes, was dewatered, and washed 3 times with 100 cm³ of water, and twice with 100 cm³ of ethanol. 33 g of 6,7-difluoroquinoline-3-carboxamide was obtained in the form of white crystals, which melted at 261° C.

6,7-Difluoroquinoline-3-carboxylic Acid was Prepared in the Following Manner:

A suspension of 37.7 g of ethyl 6,7-difluoroquinoline-3-carboxylate in a mixture of 20 cm³ of ethanol and 160 cm³ of a 1 N aqueous potassium hydroxide solution was stirred for 4 hours, at a temperature of 20° C. 600 cm³ of water was added to the solution and the insoluble material was extracted twice with 400 cm³ of diethyl ether. The aqueous solution was neutralized with 161 cm³ of a 1 N aqueous hydrochloric acid solution. The precipitate obtained was dewatered, washed 3 times with 150 cm³ of water, and dried under vacuum at a temperature of 50° C. 30 g of 6,7-difluoroquinoline-3-carboxylic acid was obtained in the form of white crystals, which melted at 290° C.

Ethyl 6,7-difluoroquinoline-3-carboxylate was Prepared in the Following Manner:

A solution of 52.9 g of ethyl 4-chloro-6,7-difluoroquinoline-3-carboxylate in 750 cm³ of ethanol, in the presence of 19.7 g of triethylamine, was hydrogenated at atmospheric pressure, at a temperature in the region of 20° C., for 1 hour in the presence of 3 g of 5% palladium on carbon (type D). After removing the catalyst by filtration at high temperature, being concentrated to dryness under reduced pressure (5.2 kPa) at about 50° C., the residue was taken up, with stirring, in 1.2 liters of water, dewatered, and washed 3 times with 200 cm³ of water. It was dissolved in 1 liter of diethyl ether; the ethereal extracts were washed twice with 100 cm³ of water and were dried over sodium sulphate. After filtration and concentration under reduced pressure (5.2 kPa), the compound obtained was recrystallized from 600 cm³ of diisopropyl ether. 42.8 g of ethyl 6,7-difluoroquinoline-3-carboxylate was obtained in the form of white crystals, which melted at 135° C.

Ethyl 4-chloro-6,7-difluoroquinoline-3-carboxylate was Prepared in the Following Manner:

A suspension of 58.3 g of ethyl 6,7-difluoro-4-oxoquinoline-3-carboxylate in 490 g of phosphorus oxychloride was heated at 95° C. for 5 hours with stirring. After evaporation to dryness under reduced pressure (5.2 kPa), the viscous residue obtained was supplemented with 500 cm³ of ice-cold water and decomposed by slow addition of a saturated aqueous potassium carbonate solution up to pH 8. The insoluble material formed was extracted twice with 400 cm³ of dichloromethane. The organic extracts obtained were dried over sodium sulphate in the presence of animal charcoal, filtered, and concentrated under reduced pressure (5.2 kPa). The residue obtained was recrystallized from 800 cm³ of hexane. 53 g of ethyl 4-chloro-6,7-difluoroquinoline-3-carboxylate was obtained in the form of white crystals, which melted at 111° C.

Ethyl 6,7-difluoro-4-oxoquinoline-3-carboxylate was prepared as described in Angeles de la Cruz et al., Tetrahedron 48, 29, pp. 6135–6150 (1992), which preparatory method is incorporated herein by reference.

EXAMPLE 3

8-Chloro-7-fluoro-9-[4-(3-chloro-4-fluorophenyl) piperazin-1-yl]-4-methyl-1-oxo-1,4-dihydrobenzo[f][1,7] naphthyridine-2-carboxylic Acid was Prepared in the Following Manner:

A stirred suspension of 0.16 g of ethyl 8-chloro-7-fluoro-9-[4-(3-chloro-4-fluorophenyl)piperazin-1-yl]-4-methyl-1-oxo-1,4-dihydrobenzo[f][1,7]naphthyridine-2-carboxylate in 4 cm³ of ethanol, 0.33 cm³ of 1 N aqueous potassium hydroxide solution, and 2.5 cm³ of distilled water were heated in the region of 100° C. for 3 hours. The mixture obtained was acidified at this same temperature with 0.5 cm³ of 1 N aqueous acetic acid.

After cooling, the insoluble material was dewatered, and then washed 3 times with 20 cm³ of water, once with 10 cm³ of ethanol, and 3 times with 10 cm³ of diisopropyl ether. 0.12 g of 8-chloro-7-fluoro-9-[4-(3-chloro-4-fluorophenyl) piperazin-1-yl]-4-methyl-1-oxo-1,4-dihydrobenzo[f][1,7] naphthyridine-2-carboxylic acid was obtained in the form of a yellow solid, which melted at more than 260° C.

Ethyl 8-chloro-7-fluoro-9-[4-(3-chloro-4-fluorophenyl) piperazin-1-yl]-4-methyl-1-oxo-1,4-dihydrobenzo[f][1,7] naphthyridine-2-carboxylate was Prepared in the Following Manner:

A stirred suspension of 1.5 g of ethyl 8-chloro-7,9-difluoro-4-methyl-1-oxo-1,4-dihydrobenzo[f][1,7] naphthyridine-2-carboxylate and 2.3 g of I-(3-chloro-4-fluorophenyl)piperazine in 15 cm³ of dimethyl sulphoxide was heated at a temperature in the region of 100° C. for 3 hours. The reaction medium was then stirred for 15 hours at room temperature, and then 10 cm³ of ethanol was added, and the medium was heated at a temperature in the region of 100° C. for 21 hours. The reaction mixture was concentrated to dryness under reduced pressure (5.2 kPa) at 80° C. The residue obtained was taken up in 50 cm³ of ethanol. The precipitate was filtered on sintered glass, washed 3 times with 5 cm³ of ethanol, and dried. The yellow powder obtained was chromatographed on a Merck silica gel column (particle size 0.04–0.06 mm, diameter 2 cm, height 20 cm), eluted at a nitrogen pressure of 50 kPa with a mixture of dichloromethane and methanol (98/2 mixture by volume), and 50 cm³ fractions were collected. Fractions 9 to 16 were combined and then concentrated to dryness under reduced pressure (2.7 kPa). The yellow solid obtained was washed with 10 cm³ of ethanol, filtered, and dried. 0.21 g of ethyl 8-chloro-7-fluoro-9-[4-(3-chloro-4-fluorophenyl)piperazin-1-yl]-4-methyl-1-oxo-1,4-dihydrobenzo[f][1,7]-naphthyridine-2-carboxylate was obtained in the form of a yellow solid, which melted at a temperature of greater than 260° C.

Ethyl 8-chloro-7,9-difluoro-4-methyl-1-oxo-1,4-dihydrobenzo[f][1,7]-naphthyridine-2-carboxylate was prepared according to the method described in Example 1.

1-(3-Chloro-4-fluorophenyl)piperazine was Prepared in the Following Manner:

A mixture of 7.5 g of 3-chloro-4-fluorobenzene, 3.9 g of sodium tert-butoxide, 1.1 g of 1,1'-bis(diphenylphosphino) ferrocenylpalladium chloride, 2.4 g of 1,1'-bis (diphenylphosphino)ferrocene, and 300 cm³ of toluene was heated at 90° C., under a nitrogen stream, for 24 hours. The reaction mixture was cooled to room temperature and filtered on sintered glass. The filtrate was washed twice with 150 cm³ of dichloromethane, and then concentrated to dryness under reduced pressure (2.7 kPa). The residue obtained was purified by chromatography on a silica gel column (particle size 0.04–0.06 mm, diameter 7 cm, height 30 cm), at a nitrogen pressure of 50 kPa, with a mixture of dichloromethane and methanol (80/20 by volume) as eluent, and 150 cm³ fractions were collected. Fractions 22 to 29 were combined and concentrated to dryness under reduced pressure (2.7 kPa). The solid obtained was taken up in 20 cm³ of dichloromethane and distilled in a bulb oven (about 180° C. at a pressure of 0.5 mm of mercury). 2.3 g of 4-(3-chloro-4-fluorophenyl)piperazine was obtained in the form of a colorless oil.

1,1'-Bis(diphenylphosphino)ferrocenylpalladium chloride was prepared as described in T. Hayashi et al., published in J. Am. Chem. Soc., 1984,106, p.158, which preparatory method is incorporated herein by reference.

EXAMPLE 4

8-Fluoro-4-methyl-1-oxo-7-[4-(3-trifluoromethylphenyl) piperazin-1-yl]-1,4-dihydrobenzo[f][1,7]naphthyridine-2-carboxylic Acid was Prepared in the Following Manner:

A stirred suspension of 0.40 g of ethyl 8-fluoro-4-methyl-1-oxo-7-[4-(3-trifluoromethylphenyl)piperazin-1-yl]-1,4-dihydrobenzo[f][1,7]naphthyridine-2-carboxylate in 12 cm³ of ethanol, 2.25 cm³ of a 1 N aqueous potassium hydroxide solution, and 4 cm³ of water was heated in the region of 100° C. for 3 hours, and then stirred at room temperature for 48 hours. The solution obtained was acidified at this same temperature with 2.5 cm³ of a 1 N aqueous hydrochloric acid solution.

After cooling, the insoluble material was dewatered and then washed 5 times with 10 cm³ of water. 0.26 g of 8-fluoro-4-methyl-1-oxo-7-[4-(3-trifluoromethylphenyl) piperazin-1-yl]-1,4-dihydrobenzo[f][1,7]naphthyridine-2-carboxylic acid was obtained in the form of an orange-colored solid, which melted at 261° C.

Ethyl 8-fluoro-4-methyl-1-oxo-7-[4-(3-trifluoromethyl phenyl)piperazin-1-yl]-1,4-dihydrobenzo[f][1,7] naphthyridine-2-carboxylate was Prepared in the Following Manner:

A stirred suspension of 3 g of ethyl 7,8-difluoro-4-methyl-1-oxo-1,4-dihydrobenzo[f][1,7]naphthyridine-2-carboxylate and 2.6 g of 4-(3-trifluoromethyl) phenylpiperazine in 30 cm³ of dimethyl sulphoxide was heated at a temperature in the region of 100° C. for about 100 hours. The reaction mixture was treated with 300 cm³ of water and extracted 3 times with 100 cm³ of dichloromethane. The organic phase was dried over magnesium sulphate and concentrated to dryness under reduced pressure (2.7 kPa). The residue obtained was chromatographed on a Merck silica gel column (particle size 0.04–0.06 mm, diameter 5 cm, height 50 cm), eluted at an argon pressure of 100 kPa with a mixture of dichloromethane, ethyl acetate, and methanol (49/49/2 mixture by volume), and 50 cm³ fractions were collected. Fractions 29 to 47 were combined and then concentrated to dryness under reduced pressure (2.7 kPa). 0.4 g of ethyl 8-fluoro-4-methyl-1-oxo-7-[4-(3-trifluoromethylphenyl)piperazin-1-yl]-1,4-dihydrobenzo[f]

[1,7]naphthyridine-2-carboxylate was obtained in the form of a yellow solid.

Ethyl 7,8-difluoro-4-methyl-1-oxo-1,4-dihydrobenzo[f][1,7]naphthyridine-2-carboxylate was Prepared in the Following Manner:

A suspension of 35 g of ethyl 7,8-difluoro-1-oxo-1,4-dihydrobenzo[f][1,7]-naphthyridine-2-carboxylate and 31.8 g of potassium carbonate in 350 cm³ of dimethyl sulphoxide was heated, with stirring, at a temperature of 90° C. for 3 hours. After cooling to 50° C., 65 g of methyl iodide were added; the mixture was heated at 90° C. for 3 hours. After cooling to 20° C., the insoluble material was dewatered, washed 4 times with 100 cm³ of water, 3 times with 100 cm³ of ethanol, and twice with 100 cm³ of diethyl ether. 25.5 g of ethyl 7,8-difluoro-4-methyl-1-oxo-1,4-dihydrobenzo[f][1,7]naphthyridine-2-carboxylate was obtained in the form of white crystals, which melted at 320° C.

Ethyl 7,8-difluoro-1-oxo-1,4-dihydrobenzo[f][1,7]naphthyridine-2-carboxylate was Prepared in the Following Manner:

A suspension of 16 g of diethyl 7,8-difluoro-3-quinolylaminomethylidine-malonate in 110 cm³ of diphenyl ether was heated, with stirring, at a temperature of 235° C. for 30 minutes. After cooling to 50° C., 250 cm of hexane were added; the mixture was cooled to 10° C. The precipitate obtained was dewatered and washed 3 times with 150 cm³ of diethyl ether. 12.9 g of a pink solid was obtained, which melted at 307° C.

Diethyl 7,8-difluoro-3-quinolylaminomethylidinemalonate was Prepared in the Following Manner:

11.5 g of diethyl ethoxymethylidinemalonate were added to a suspension of 8.9 g of 3-amino-7,8-difluoroquinoline in 50 cm³ of toluene. The medium was heated, with stirring, at a temperature of 110° C. for 8 hours. The medium was concentrated to dryness under reduced pressure (5.2 kPa); the compound isolated was taken up, with stirring, in 150 cm³ of diisopropyl ether, dewatered and washed twice with 100 cm³ of the same solvent. 16.1 g of the compound was obtained in the form of white crystals, which melted at 164° C.

3-Amino-7,8-difluoroquinoline was Prepared in the Following Manner:

7.8 g of 7,8-difluoroquinoline-3-carboxamide were treated with an aqueous sodium hypobromite solution obtained by addition of 6.4 g of bromine to 118 cm³ of a 2 N aqueous sodium hydroxide solution. The compound after treatment was dissolved in 600 cm³ of diethyl ether; the organic extracts were washed 3 times with 50 cm³ of water and then dried over sodium sulphate in the presence of 2 g of animal charcoal. 4.9 g of 3-amino-7,8-difluoroquinoline was isolated in the form of white crystals, which melted at 161° C.

7,8-Difluoroquinoline-3-carboxamide was Prepared in the Following Manner:

51 g of thionyl chloride and 3 drops of dimethylformamide were added to a suspension of 15.5 g of 7,8-difluoroquinoline-3-carboxylic acid in 100 cm³ of chloroform. The compound isolated was suspended in 300 cm³ of dichloromethane and treated as in Example 2. 14.8 g of 7,8-difluoroquinoline-3-carboxamide was thus obtained in the form of white crystals, which melted at 250° C.

7,8-Difluoroquinoline-3-carboxylic Acid was Prepared in the Following Manner:

A suspension of 17.6 g of diethyl 7,8-difluoroquinoline-3-carboxylate in a mixture of 100 cm³ of ethanol and 90 cm³ of 1 N potassium hydroxide was stirred for 1 hour at a temperature of 60° C. After concentration under reduced pressure (5.2 kPa), the residue was dissolved in 400 cm³ of water; the insoluble material was dewatered and the alkaline extracts were neutralized with 91 cm³ of a 1 N aqueous hydrochloric acid solution. The precipitate obtained by filtration was washed 3 times with 50 cm³ of water and dried under vacuum at 50° C. 14.3 g of 7,8-difluoroquinoline-3-carboxylic acid was obtained in the form of white crystals, which melted at 275° C.

Ethyl 7,8-difluoroquinoline-3-carboxylate was Prepared in the Following Manner:

A solution of 21.9 g of ethyl 4-chloro-7,8-difluoroquinoline-3-carboxylate in 7300 cm³ of ethanol in the presence of 8.8 g of triethylamine and 2.2 g of 5% palladium on carbon was hydrogenated at atmospheric pressure for 1 hour. The solid residue obtained was recrystallized from 300 cm³ of hexane. 17.6 g of ethyl 7,8-difluoroquinoline-3-carboxylate was obtained in the form of white crystals, which melted at 118° C.

Ethyl 4-chloro-7,8-difluoroquinoline-3-carboxylate was Prepared in the Following Manner:

A suspension of 26 g of ethyl 7,8-difluoro-4-oxoquinoline-3-carboxylate in 212 g of phosphorus oxychloride was heated at 95° C. for 4 hours, with stirring. After treatment, 27.3 g of ethyl 4-chloro-7,8-difluoroquinoline-3-carboxylate was obtained in the form of a white solid, which melted at 114° C.

Ethyl 7,8-difluoro-4-oxoquinoline-3-carboxylate was Prepared in the Following Manner:

A suspension of 32.7 g of diethyl 2,3-difluorophenylaminomethylidinemalonate in 220 cm³ of diphenyl ether was heated, with stirring, at a temperature of 235° C. for 2.5 hours. After cooling to 50° C., 250 cm³ of hexane was added. The mixture was cooled to 10° C.; the precipitate obtained was dewatered and washed 3 times with 200 cm³ of diethyl ether. 26.2 g of ethyl 7,8-difluoro-4-oxoquinoline-3-carboxylate was obtained in the form of a white solid, which melted at 270° C.

Diethyl 2,3-difluorophenylaminomethylidinemalonate was Prepared in the Following Manner:

A mixture of 15.1 g of 2,3-difluoroaniline and 26 g of diethyl ethoxymethylidinemalonate was heated, with stirring, at a temperature of 115° C. for 2.5 hours. After cooling, the solid obtained was recrystallized from 200 cm³ of hexane. 32.7 g of diethyl 2,3-difluorophenylaminomethylidinemalonate was obtained in the form of white crystals, which melted at 97° C.

EXAMPLE 5

9-(3,3-Dimethylpiperidino)-8-fluoro-4-methyl-1-oxo-1,4-dihydrobenzo[f][1,7]naphthyridine-2-carboxylic Acid was Prepared in the Following Manner:

2.3 cm³ of 1 N aqueous potassium hydroxide were added, with stirring, to a suspension of 0.83 g of ethyl 9-(3,3-dimethylpiperidino-1-yl)-8-fluoro-4-methyl-1-oxo-1,4-dihydrobenzo[f][1,7]naphthyridine-2-carboxylate in 15 cm³ of ethanol and 15 cm³ of water. The mixture was heated for 2 hours at about 100° C. The solution was acidified by addition of 2.3 cm³ of 1 N aqueous hydrochloric acid. After cooling, the precipitate was dewatered, washed three times with 10 cm³ of water, three times with 10 cm³ of ethanol, and three times with 10 cm³ of diethyl ether. The solid was dried at about 50° C. at a pressure of 1 kPa for 4 hours. 0.75 g of 9-(3,3-dimethylpiperidin-1-yl)-8-fluoro-4-methyl-1- oxo-1,4-dihydrobenzo[f][1,7]naphthyridine-2-carboxylic acid was obtained in the form of a yellow solid, which melted at around 292–295° C.

Ethyl 9-(3,3-dimethylpiperidino)-8-fluoro-4-methyl-1-oxo-1,4-dihydrobenzo[f][1,7]naphthyridine-2-carboxylate and ethyl 8-(3,3-dimethylpiperidino)-9-fluoro-4-methyl-1-oxo-1,4-dihydrobenzo[f][1,7]naphthyridine-2-carboxylate were Prepared in the Following Manner:

A suspension of 2 g of ethyl 8,9-difluoro-4-methyl-1-oxo-1,4-dihydrobenzo[f][1,7]naphthyridine-2-carboxylate and 3.23 cm³ of 3,3-dimethylpiperidine in 40 cm³ of dimethyl sulphoxide was heated at a temperature in the region of 80° C. for 72 hours. After cooling to about 200° C., 200 cm³ of water was added to the reaction mixture. The precipitate obtained was dewatered and washed with 25 cm³ of water. The solid was taken up in 100 cm³ of dichloromethane, the residual water was decanted off; the organic solution was dried over magnesium sulphate and concentrated under reduced pressure (5 kPa) at about 40° C. 2.67 g of a mixture containing ethyl 9-(3,3-dimethylpiperidin-1-yl)-8-fluoro-4-methyl-1-oxo-1,4-dihydrobenzo[f][1,7]naphthyridine-2-carboxylate and ethyl 8-(3,3-dimethylpiperidin-1-yl)-9-fluoro-4-methyl-1-oxo-1,4-dihydrobenzo[f][1,7]naphthyridine-2-carboxylate was obtained. This mixture was purified by flash chromatography on silica gel (particle size 20–45 µm, diameter 10 cm, height 60 cm) at a pressure of 80 kPa, eluted with a mixture containing 99% dichloromethane and 1% methanol, and 70 cm³ fractions were collected. After concentration of fractions 16 to 39 under reduced pressure (5 kPa) at about 50° C., 0.85 g of ethyl 9-(3,3-dimethylpiperidin-1-yl)-8-fluoro-4-methyl-1-oxo-1,4-dihydrobenzo[f][1,7]naphthyridine-2-carboxylate was obtained in the form of a yellow solid, which melted at around 218–220° C.

After concentration of fractions 104 to 216 under reduced pressure (5 kPa), at about 50° C., 0.5 g of ethyl 8-(3,3-dimethylpiperidin-1-yl)-9-fluoro-4-methyl-1-oxo-1,4-dihydrobenzo[f][1,7]naphthyridine-2-carboxylate was obtained in the form of a yellow solid, which melted at about 198–200° C.

Ethyl 8,9-difluoro-4-methyl-1-oxo-1,4-dihydrobenzo[f][1,7]naphthyridine-2-carboxylate was prepared according to the method described in Example 2.

EXAMPLE 6

8-(3,3-Dimethylpiperidino)-9-fluoro-4-methyl-1-oxo-1,4-dihydrobenzo[f][1,7]naphthyridine-2-carboxylic Acid was Prepared in the Following Manner:

1.4 cm³ of 1 N aqueous potassium hydroxide was added, with stirring, to a suspension of 0.5 g of ethyl 8-(3,3-dimethylpiperidin-1-yl)-9-fluoro-4-methyl-1-oxo-1,4-dihydrobenzo[f][1,7]naphthyridine-2-carboxylate in 15 cm³ of ethanol and 15 cm³ of water. The mixture was heated at about 100° C. for one hour. The suspension obtained was acidified by addition of 1.4 cm³ of 1 N aqueous hydrochloric acid. After cooling, the precipitate was dewatered, washed three times with 10 cm³ of water, three times with 10 cm³ of ethanol, and three times with 10 cm³ of ether. The solid was dried at about 80° C. at 1 kPa for 4 hours. 0.38 g of 8-(3,3-dimethylpiperidin-1-yl)-9-fluoro-4-methyl-1-oxo-1,4-dihydrobenzo[f][1,7]naphthyridine-2-carboxylic acid was obtained in the form of a yellow solid, which melted with decomposition at about 286–7° C.

The preparation of ethyl 8-(3,3-dimethylpiperidin-1-yl)-9-fluoro-4-methyl-1-oxo-1,4-dihydrobenzo[f][1,7]naphthyridine-2-carboxylate was described in Example 5.

EXAMPLE 7

7-Fluoro-8-[4-(3-fluoro-4-methyl phenyl)piperazin-1-yl]-4-methyl-1-oxo-1,4-dihydrobenzo[f][1,7]naphthyridine-2-carboxylic Acid was Prepared in the Following Manner:

A stirred suspension of 1.0 g of ethyl 7-fluoro-8-[4-(3-fluoro-4-methylphenyl)piperazin-1-yl]-4-methyl-1-oxo-1,4-dihydrobenzo[f][1,7]naphthyridine-2-carboxylate in 20 cm³ of acetic acid at 100%, and 2 cm³ of hydrochloric acid at 37% was heated in the region of 110° C. for 7 hours. The solution obtained was concentrated under reduced pressure (20 kPa) and the residue was taken up three times in 30 cm³ of water at about 80° C.

The insoluble material was dewatered, then washed 3 times with 30 cm³ of water, 3 times with 30 cm³ of ethanol, and 3 times with 20 cm³ of diethyl ether. 0.79 g of 7-fluoro-8-[4-(3-fluoro-4-methylphenyl)piperazin-1-yl]-4-methyl-1-oxo-1,4-dihydrobenzo[f][1,7]naphthyridine-2-carboxylic acid was obtained in the form of a yellow solid which melted at more than 300° C.

Ethyl 7-fluoro-8-[4-(3-fluoro-4-methylphenyl)piperazin-1-yl]-4-methyl-1-oxo-1,4-dihydrobenzo[f][1,7]naphthyridine-2-carboxylate was Prepared as Follows:

A stirred suspension of 3 g of ethyl 7,8-difluoro-4-methyl-1-oxo-1,4-dihydrobenzo[f][1,7]naphthyridine-2-carboxylate and 3.9 g of 1-(3-fluoro-4-methylphenyl)piperazine in 30 cm³ of dimethyl sulphoxide was heated at a temperature in the region of 100° C. for about 100 hours. The reaction mixture was treated with 150 cm³ of water in the region of 10° C. and the precipitate was taken up in 100 cm³ of dichloromethane, dried with 10 g of magnesium sulphate and concentrated to dryness under reduced pressure (20 kPa). The yellow powder obtained was chromatographed on a Merck silica gel column (particle size 0.04–0.06 mm, diameter 3 cm, height 80 cm), eluted at an argon pressure of 1 bar with a mixture of dichloromethane and methanol (98/2 mixture by volume), and 200 cm³ fractions were collected. Fractions 16 to 23 were combined and then concentrated to dryness under reduced pressure (2.7 kPa). The yellow solid obtained was washed with 10 cm³ of diethyl ether, filtered and dried. 1.1 g of ethyl 7-fluoro-8-[4-(3-fluoro-4-methylphenyl)piperazin-1-yl]-4-methyl-1-oxo-1,4-dihydrobenzo[f][1,7]naphthyridine-2-carboxylate was obtained in the form of a yellow solid, which melted at a temperature in the region of 290° C.

Ethyl 7,8-difluoro-4-methyl-1-oxo-1,4-dihydrobenzo[f][1,7]naphthyridine-2-carboxylate was prepared as described in Example 4.

1-(3-fluoro-4-methylphenyl)piperazine was prepared according to the method described in German patent no. DE 1019308 and U.S. Pat. No. 2,830,056, which preparatory method is incorporated herein by reference.

EXAMPLE 8

8-Fluoro-7-[4-hydroxy-4-(3-trifluoromethylphenyl)piperidin-1-yl]-4-methyl-1-oxo-1,4-dihydrobenzo[f][1,7]naphthyridine-2-carboxylic Acid was Prepared in the Following Manner:

1.02 cm³ of 1 N aqueous potassium hydroxide was added, with stirring, to a suspension of 0.46 g of ethyl 8-fluoro-7-[4-hydroxy-4-(3-trifluoromethylphenyl)piperidin-1-yl]-4-methyl-1-oxo-1,4-dihydrobenzo[f][1,7]naphthyridine-2-carboxylate in 5 cm³ of ethanol and 4 cm³ of water. The mixture was heated at about 80° C. for 2 hours and then evaporated to dryness. The residue was dissolved in 20 cm³ of water, the aqueous phase was washed with 20 cm³ of dichloromethane, acidified with 0.06 cm³ of acetic acid and then extracted 3 times with 50 cm³ of dichloromethane. The organic phase was dried over magnesium sulphate and concentrated to dryness under reduced pressure (20 kPa). The residue obtained was washed twice with 5 cm³ of diisopropyl ether and dried. 0.22 g of 8-fluoro-7-[4-hydroxy-4-(3-trifluoromethylphenyl)piperidin-1-yl]-4-methyl-1-oxo-1,4-dihydrobenzo[f][1,7]naphthyridine-2-carboxylic acid was obtained in the form of a yellow solid, which melted at 245° C.

Ethyl 8-fluoro-7-[4-hydroxy-4-(3-trifluoromethylphenyl)piperidin-1-yl]-4-methyl-1-oxo-1,4-dihydrobenzo[f][1,7]naphthyridine-2-carboxylate and ethyl 7-fluoro-8-[4-hydroxy-4-(3-trifluoromethylphenyl)piperidin-1-yl]-4-methyl-1-oxo-1,4-dihydrobenzo[f][1,7]naphthyridine-2-carboxylate was Prepared in the Following Manner:

A suspension of 2.23 g of ethyl 7,8-difluoro-4-methyl-1-oxo-1,4-dihydrobenzo[f][1,7]naphthyridine-2-carboxylate, 3 g of 4-hydroxy-4-(3-trifluoromethylphenyl)piperidine hydrochloride, and 3 cm³ of triethylamine in 20 cm³ of dimethyl sulphoxide was heated at a temperature in the region of 100° C. for 24 hours, and then a further 3 g of 4-hydroxy-4-(3-trifluoro-methylphenyl)piperidine hydrochloride and 3 cm³ of triethylamine in 5 cm³ of dimethyl sulphoxide were added and the medium was heated at a temperature in the region of 100° C. for 72 hours. After cooling to about 20° C., the reaction medium was filtered, the filtrate was treated with 100 g of crushed ice and then 100 cm³ of water, and then extracted with 200 cm³ of dichloromethane. The organic phase was dried over magnesium sulphate and concentrated under reduced pressure (5 kPa) at about 40° C. 3.93 g of a mixture of ethyl 8-fluoro-7-[4-hydroxy-4-(3-trifluoromethylphenyl)-piperidin-1-yl]-4-methyl-1-oxo-1,4-dihydrobenzo[f][1,7]naphthyridine-2-carboxylate and ethyl 7-fluoro-8-[4-hydroxy-4-(3-trifluoromethylphenyl)piperidin-1-yl]-4-methyl-1-oxo-1,4-dihydro-benzo[f][1,7]naphthyridine-2-carboxylate was obtained. This mixture was purified by flash chromatography on silica gel (particle size 20–45 μm, diameter 5.1 cm, weight of silica 393 g) under 50 kPa of argon, eluted with a mixture containing 98% dichloromethane and 2% ethanol, and 50 cm³ fractions were collected. After concentration of fractions 55 to 66 under reduced pressure (5 kPa) at about 50° C., 0.34 g of ethyl 8-fluoro-7-[4-hydroxy-4-(3-trifluoromethylphenyl)piperidin-1-yl]-4-methyl-1-oxo-1,4-dihydrobenzo[f][1,7]naphthyridine-2-carboxylate was obtained in the form of a yellow solid, which melted at around 122° C.

After concentration of fractions 112 to 149 under reduced pressure (5 kPa) at about 50° C., 0.3 g of ethyl 7-fluoro-8-[4-hydroxy-4-(3-trifluoromethylphenyl)piperidin-1-yl]-4-methyl-1-oxo-1,4-dihydrobenzo[f][1,7]naphthyridine-2-carboxylate was obtained in the form of a yellow solid, which melted at more than 260° C.

Ethyl 7,8-difluoro-4-methyl-1-oxo-1,4-dihydrobenzo[f][1,7]naphthyridine-2-carboxylate was prepared according to the method described in Example 4.

EXAMPLE 9

7-Fluoro-8-[4-hydroxy-4-(3-trifluoromethylphenyl)piperidin-1-yl]-4-methyl-1-oxo-1,4-dihydrobenzo[f][1,7]naphthyridine-2-carboxylic Acid was Prepared in the Following Manner:

0.86 cm³ of 1 N aqueous potassium hydroxide was added, with stirring, to a suspension of 0.39 g of ethyl 7-fluoro-8-[4-hydroxy-4-(3-trifluoromethylphenyl)piperidin-1-yl]-4-methyl-1-oxo-1,4-dihydrobenzo[f][1,7]naphthyridine-2-carboxylate in 4.5 cm³ of ethanol and 3.5 cm³ of water. The mixture was heated at about 80° C. for 3 hours, and then after cooling, 20 cm³ of water were added and then the medium was acidified with 0.05 cm³ of acetic acid. The precipitate was filtered off, dewatered, washed with 2 cm³ of isopropanol and then washed twice with 2 cm³ of diisopropyl ether and dried. 0.25 g of 7-fluoro-8-[4-hydroxy-4-(3-trifluoromethylphenyl)piperidin-1-yl]-4-methyl-1-oxo-1,4-dihydrobenzo[f][1,7]naphthyridine-2-carboxylic acid was obtained in the form of a yellow solid, which melted above 260° C.

Ethyl 7-fluoro-8-[4-hydroxy-4-(3-trifluoromethylphenyl)piperidin-1-yl]-4-methyl-1-oxo-1,4-dihydrobenzo[f][1,7]naphthyridine-2-carboxylate was prepared according to the method described in Example 8.

EXAMPLE 10

9-[2-Anilinomethyl-(2S)-pyrrolidino]-8-fluoro-4-methyl-1-oxo-1,4-dihydrobenzo[f][1,7]naphthyridine-2-carboxylic Acid was Prepared in the Following Manner:

3.4 cm³ of 1 N aqueous potassium hydroxide was added, with stirring, to a suspension of 0.66 g of ethyl (S)-8-fluoro-4-methyl-1-oxo-9-(2-phenylaminomethylpyrrolidin-1-yl)-1,4-dihydrobenzo[f][1,7]naphthyridine-2-carboxylate in 15 cm³ of ethanol and 10 cm³ of water. The mixture was heated at about 100° C. for 24 hours. The suspension obtained was acidified by addition of 3.4 cm³ of 1 N aqueous hydrochloric acid. After cooling, the solid was dewatered and washed three times with 50 cm³ of water and dried at about 100° C. for 4 hours at a pressure of 1 kPa. 1 g of (S)-8-fluoro-4-methyl-1-oxo-9-(2-phenylaminomethylpyrrolidin-1-yl)-1,4-dihydrobenzo[f][1,7]naphthyridine-2-carboxylic acid was obtained in the form of an orange-colored solid, which melted at around 250° C.

Ethyl 9-[2-anilinomethyl-(2S)-pyrrolidino]-8-fluoro-4-methyl-1-oxo-1,4-dihydrobenzo[f][1,7]naphthyridine-2-carboxylate was Prepared in the Following Manner:

A suspension of 2.4 g of ethyl 8,9-difluoro-4-methyl-1-oxo-1,4-dihydrobenzo[f][1,7]naphthyridine-2-carboxylate and 3.25 g of (S)-2-(phenylaminomethyl)pyrrolidine in 50 cm³ of dimethyl sulphoxide was heated at a temperature in the region of 80° C. for 96 hours. After cooling to about 20° C., 200 cm³ of water was added to the reaction mixture. The precipitate obtained was dewatered and washed with 25 cm³ of water. The solid (3.4 g) was purified by flash chromatography on silica gel (particle size 20–45 μm, diameter 4 cm, height 40 cm) under 80 kPa, eluted with a mixture containing 99% dichloromethane and 1% ethanol, and 30 cm³ fractions were collected. After concentration of fractions 40 to 60 under reduced pressure (5 kPa) at about 50° C., 1.5 g of a solid was obtained which, after recrystallization from 100 cm³ of isopropanol, produced 1.3 g of ethyl (S)-8-fluoro-4-methyl-1-oxo-9-(2-phenylaminomethylpyrrolidin-1-yl)-1,4-dihydrobenzo[f][1,7]naphthyridine-2-carboxylate in the form of a yellow solid, which melted at around 170° C.

Ethyl 8,9-difluoro-4-methyl-1-oxo-1,4-dihydrobenzo[f][1,7]naphthyridine-2-carboxylate was prepared according to the method described in Example 2.

EXAMPLE 11

9-[3-(4-Benzyloxy-3-methoxyphenyl)piperazin-1-yl]-8-fluoro-4-methyl-1-oxo-1,4-dihydrobenzo[f][1,7]

naphthyridine-2-carboxylic Acid was Prepared in the Following Manner:

A stirred suspension of 0.68 g of ethyl 9-[3-(4-benzyloxy-3-methoxyphenyl)-4-trifluoromethylacetylpiperazin-1-yl]-8-fluoro-4-methyl-1-oxo-1,4-dihydrobenzo[f][1,7]naphthyridine-2-carboxylate in 6.8 cm³ of water, 20.4 cm³ of ethanol and 2.95 cm³ of 1 N aqueous potassium hydroxide was heated in the region of 100° C. for 4 hours. The ethanol was removed under reduced pressure (5 kPa) at about 50° C., 100 cm³ of water was added to the solution obtained, the medium was filtered and then the filtrate was acidified with 2 cm³ of a 1 N aqueous hydrochloric acid solution.

After heating for 1 hour at 65° C. and then cooling, the insoluble material was dewatered and then washed 3 times with 20 cm³ of water, 3 times with 20 cm³ of ethanol, and 3 times with 30 cm³ of pentane. After drying, 0.46 g of 9-[3-(4-benzyloxy-3-methoxyphenyl)piperazin-1-yl]-8-fluoro-4-methyl-1-oxo-1,4-dihydrobenzo[f][1,7]naphthyridine-2-carboxylic acid was obtained in the form of a solid, which melted at 280° C.

Ethyl 9-[3-(4-benzyloxy-3-methoxyphenyl)-4-trifluoromethylacetylpiperazin-1-yl]-8-fluoro-4-methyl-1-oxo-1,4-dihydrobenzo[f][1,7]naphthyridine-2-carboxylate was Prepared in the Following Manner:

A suspension of 2.38 g of ethyl 8,9-difluoro-4-methyl-1-oxo-1,4-dihydrobenzo[f][1,7]naphthyridine-2-carboxylate, 2.23 g of 2-(4-benzyloxy-3-methoxyphenyl)piperazine and 12.6 cm³ of triethylamine in 50 cm³ of dimethyl sulphoxide was heated at a temperature in the region of 90° C. for 170 hours.

The cooled mixture was poured over 500 cm³ of ice-cold water, with stirring. The insoluble material was extracted 5 times with 100 cm³ of dichloromethane. The organic phase was dried over magnesium sulphate, concentrated under reduced pressure (5 kPa) at about 40° C. The residue obtained (3.66 g) was dissolved in 70 cm³ of dichloromethane, 4.3 cm³ of trifluoroacetic anhydride was added to this solution and the reaction mixture was stirred for 24 hours at room temperature. 5 g of sodium hydrogen carbonate and 100 cm³ of water were then added and the medium was extracted with dichloromethane. The organic phases were combined and then after drying over magnesium sulphate, the medium was concentrated under reduced pressure (5 kPa) at about 40° C. The residue obtained was purified three times by chromatography on a silica gel column (particle size 0.04–0.063, diameter 6 cm, height 40 cm) under 50 kPa of argon, eluted with a mixture of dichloromethane and ethanol (99/1 by volume). After concentration of the least polar fractions to dryness under reduced pressure (5 kPa) at about 40° C., 0.69 g of ethyl 9-[3-(4-benzyloxy-3-methoxyphenyl)-4-trifluoromethylacetylpiperazin-1-yl]-8-fluoro-4-methyl-1-oxo-1,4-dihydrobenzo[f][1,7]naphthyridine-2-carboxylate was obtained in the form of a yellow solid, which melted at 154° C.

Ethyl 8,9-difluoro-4-methyl-1-oxo-1,4-dihydrobenzo[f][1,7]naphthyridine-2-carboxylate was prepared according to the method described in Example 2.

EXAMPLE 12

8-Fluoro-9-[4-hydroxy-4-(3-trifluoromethyl phenyl)piperidino]-4-methyl-1-oxo-1,4-dihydrobenzo[f][1,7]naphthyridine-2-carboxylic Acid was Prepared in the Following Manner:

A stirred suspension of 1.09 g of ethyl 8-fluoro-9-[4-hydroxy-4-(3-trifluoromethylphenyl)piperidin-1-yl]-4-methyl-1-oxo-1,4-dihydrobenzo[f][1,7]naphthyridine-2-carboxylate in 8 cm³ of water, 10 cm³ of ethanol, and 2.4 cm³ of a 1 N aqueous potassium hydroxide solution was heated in the region of 100° C. for 1 hour and 30 minutes. The solution obtained was acidified at this same temperature with 2.5 cm³ of a 1 N aqueous acetic acid solution.

After cooling, the insoluble material was dewatered and then washed twice with 10 cm³ of water, once with 5 cm³ of ethanol, and twice with 5 cm³ of diethyl ether. After recrystallization from 5 cm³ of dimethylformamide, 0.72 g of 8-fluoro-9-[4-hydroxy-4-(3-trifluoromethylphenyl)piperidin-1-yl]-4-methyl-1-oxo-1,4-dihydrobenzo[f][1,7]naphthyridine-2-carboxylic acid was obtained in the form of a yellow solid, which melted at 300° C.

Ethyl 8-fluoro-9-[4-hydroxy-4-(3-trifluoromethylphenyl)piperidino]-4-methyl-1-oxo-1,4-dihydrobenzo[f][1,7]naphthyridine-2-carboxylate was Prepared in the Following Manner:

A suspension of 3.7 g of 4-[3-(trifluoromethyl)phenyl]-4-piperidinol hydrochloride in 50 cm³ of dimethyl sulphoxide was stirred at a temperature in the region of 25° C. with 2.8 cm³ of triethylamine, for 10 minutes. After addition of 2 g of ethyl 8,9-difluoro-4-methyl-1-oxo-1,4-dihydrobenzo[f][1,7]naphthyridine-2-carboxylate, the mixture was heated at 100° C. for 170 hours.

The cooled mixture was poured over about 150 cm³ of ice-cold water, with stirring. The insoluble material was extracted with respectively 200, 100, and 50 cm³ of dichloromethane. After cooling the organic phases, the precipitate obtained was filtered. The filtrate was washed twice with 200 cm³ of water and then dried over magnesium sulphate and concentrated under reduced pressure (5 kPa) at about 40° C. The residue obtained was purified by chromatography on a silica gel column (particle size 0.04–0.063, diameter 6 cm, height 40 cm) at atmospheric pressure, eluted with a mixture of dichloromethane and ethanol (95/5 by volume) and 25 cm³ fractions were collected. Fractions 45 to 60 were concentrated to dryness under reduced pressure (5 kPa) at about 40° C. After washing with 20 cm³ of diethyl ether and dewatering, 1.10 g of ethyl 8-fluoro-9-[4-hydroxy-4-(3-trifluoromethyl phenyl)piperidin-1-yl]-4-methyl-1-oxo-1,4-dihydrobenzo[f][1,7]naphthyridine-2-carboxylate was obtained in the form of a yellow solid, which melted at 262° C.

Ethyl 8,9-difluoro-4-methyl-1-oxo-1,4-dihydrobenzo[f][1,7]naphthyridine-2-carboxylate was prepared according to the method described in Example 2.

EXAMPLE 13

8-Fluoro-9-[4-(3-methoxyphenyl)-3-methylpiperazin-1-yl]-4-methyl-1-oxo-1,4-dihydrobenzo[f][1,7]naphthyridine-2-carboxylic Acid was Prepared in the Following Manner:

2.4 cm³ of 1 N aqueous potassium hydroxide was added, with stirring, to a suspension of 1 g of ethyl 8-fluoro-9-[4-(3-methoxyphenyl)-3-methylpiperazin-1-yl]-4-methyl-1-oxo-1,4-dihydrobenzo[f][1,7]naphthyridine-2-carboxylate in 10 cm³ of ethanol and 20 cm³ of water heated to a temperature in the region of 50° C. The mixture was heated in the region of 100° C. for 2 hours and 30 minutes.

The solution obtained was acidified at 100° C. with 2.5 cm³ of a 1 N aqueous hydrochloric acid solution. After cooling, the insoluble material was dewatered and then washed twice with 10 cm³ of water. After dissolution of the solid obtained in about 150 cm³ of dichloromethane and then decantation of the residual water, the solution was dried over magnesium sulphate and then concentrated under reduced pressure (5 kPa) at about 40° C. The solid obtained was taken up in about 30 cm³ of diethyl ether, dewatered and air-dried. 0.88 g of 8-fluoro-9-[4-(3-methoxyphenyl)-3-methylpiperazin-1-yl]-4-methyl-1-oxo-1,4-dihydrobenzo[f][1,7]naphthyridine-2-carboxylic acid was obtained in the form of a yellow solid, which melted at 285° C.

Ethyl 8-fluoro-9-[4-(3-methoxyphenyl)-3-methylpiperazin-1-yl]-4-methyl-1-oxo-1,4-dihydrobenzo[f][1,7]naphthyridine-2-carboxylate was Prepared in the Following Manner:

A suspension of 2 g of ethyl 8,9-difluoro-4-methyl-1-oxo-1,4-dihydrobenzo[f][1,7]naphthyridine-2-carboxylate and 2.85 g of 1-(3-methoxyphenyl)-2-methylpiperazine in 50 cm³ of dimethyl sulphoxide was heated, with stirring, at a temperature in the region of 100° C. After 230 hours, an additional 1.45 g of 1-(3-methoxyphenyl)-2-methylpiperazine was added.

After heating for 170 hours, the mixture was cooled and then poured over about 200 cm³ of ice-cold water. The insoluble material was dewatered and washed twice with 20 cm³ of water. After dissolution of the solid obtained in 50 cm³ of dichloromethane, the solution obtained was washed once with 25 cm³ of water, decanted off, dried over magnesium sulphate and then concentrated under reduced pressure (5 kPa) at about 40° C. The residue obtained was purified by chromatography on a silica gel column (particle size 0.04–0.063 mm; diameter 6 cm, height 50 cm) at atmospheric pressure, eluted with a mixture of dichloromethane and ethanol (98/2 by volume) and 30 cm³ fractions were collected. Fractions 50 to 70 were concentrated to dryness under reduced pressure (5 kPa) at about 40° C. 1 g of ethyl 8-fluoro-9-[4-(3-methoxyphenyl)-3-methylpiperazin-1-yl]-4-methyl-1-oxo-1,4-dihydrobenzo[f][1,7]naphthyridine-2-carboxylate was obtained in the form of a yellow solid, which melted at 226° C.

Ethyl 8,9-difluoro-4-methyl-1-oxo-1,4-dihydrobenzo[f][1,7]naphthyridine-2-carboxylate was prepared according to the method described in Example 2.

EXAMPLE 14

9-[3-(3,4-Dimethylphenyl)piperazin-1-yl]-8-fluoro-4-methyl-1-oxo-1,4-dihydrobenzo[f][1,7]naphthyridine-2-carboxylic Acid was Prepared in the Following Manner:

A stirred suspension of 1.47 g of ethyl 9-[3-(3,4-dimethylphenyl)piperazin-1-yl]-8-fluoro-4-methyl-1-oxo-1,4-dihydrobenzo[f][1,7]naphthyridine-2-carboxylate in 25 cm³ of ethanol, 3.60 cm³ of 1 N aqueous potassium hydroxide and 15 cm³ of water was heated in the region of 100° C. for 4 hours. The reaction mixture was filtered, evaporated to dryness, the residue was suspended in 100 cm³ of water, the medium was acidified with 3.5 cm³ of a 1 N aqueous hydrochloric acid solution, 10 cm³ of ethanol was added, the medium was heated to 100° C. and filtered at high temperature. The residue was washed 3 times with 25 cm³ of water and then with 10 cm³ of ethanol. 0.98 g of 9-[3-(3,4-dimethylphenyl)piperazin-1-yl]-8-fluoro-4-methyl-1-oxo-1,4-dihydrobenzo[f][1,7]naphthyridine-2-carboxylic acid was obtained in the form of a yellow solid, which melted at 325° C.

Ethyl 9-[3-(3,4-dimethyl phenyl)piperazin-1-yl]-8-fluoro-4-methyl-1-oxo-1,4-dihydrobenzo[f][1,7]naphthyridine-2-carboxylate was Prepared in the Following Manner:

A stirred suspension of 2.5 g of ethyl 8,9-difluoro-4-methyl-1-oxo-1,4-dihydrobenzo[f][1,7]naphthyridine-2-carboxylate and 2.6 g of 2-(3,4-dimethylphenyl)piperazine in 45 cm³ of dimethyl sulphoxide was heated at a temperature in the region of 100° C. for about 100 hours. The reaction mixture was treated with 400 cm³ of water and filtered. The residue obtained was chromatographed on a Merck silica gel column (particle size 0.04–0.06 mm, diameter 5.5 cm, height 45 cm), eluted at an argon pressure of 120 kPa with a mixture of dichloromethane and ethanol (92/8 mixture by volume) and 50 cm³ fractions were collected. Fractions 37 to 80 were combined and then concentrated to dryness under reduced pressure (2.7 kPa). 1.61 g of ethyl 9-[3-(3,4-dimethylphenyl)piperazin-1-yl]-8-fluoro-4-methyl-1-oxo-1,4-dihydrobenzo[f][1,7]naphthyridine-2-carboxylate was obtained in the form of a yellow solid, which melted at 290° C.

Ethyl 8,9-difluoro-4-methyl-1-oxo-1,4-dihydrobenzo[f][1,7]naphthyridine-2-carboxylate was prepared according to the method described in Example 2.

EXAMPLE 15

9-Fluoro-8-[4-(4-fluorophenyl)piperazin-1-yl]-4-methyl-1-oxo-1,4-dihydrobenzo[f][1,7]naphthyridine-2-carboxylic Acid was Prepared in the Following Manner:

A suspension of 0.70 g of ethyl 9-fluoro-8-[4-(4-fluorophenyl)piperazin-1-yl]-4-methyl-1-oxo-1,4-dihydrobenzo[f][1,7]naphthyridine-2-carboxylate in a mixture of 250 cm³ of ethanol at 40% and 4 cm³ of a 1 N aqueous potassium hydroxide solution was heated, with stirring, for 8 hours at a temperature of 80° C. After cooling to a temperature of 60° C., the light insoluble material was removed by filtration. The solution was neutralized with 4.1 cm³ of a 1 N aqueous hydrochloric acid solution; the insoluble material formed was dewatered, washed 3 times with 20 cm³ of water and twice with 20 cm³ of ethanol and dried under vacuum at 100° C. 0.56 g of 9-fluoro-8-[4-(4-fluorophenyl)piperazin-1-yl]-4-methyl-1-oxo-1,4-dihydrobenzo[f][1,7]naphthyridine-2-carboxylic acid was obtained in the form of yellow crystals, which melted at 346° C.

Ethyl 9-fluoro-8-[4-(4-fluorophenyl)piperazin-1-yl]-4-methyl-1-oxo-1,4-dihydrobenzo[f][1,7]naphthyridine-2-carboxylate was Prepared in the Following Manner:

A suspension of 1.5 g of ethyl 8,9-difluoro-4-methyl-1-oxo-1,4-dihydrobenzo[f][1,7]naphthyridine-2-carboxylate and 1.7 g of 1-(4-fluorophenyl)piperazine in 30 cm³ of dimethyl sulphoxide was heated, with stirring, at a temperature of 90° C. for 4 days. After cooling to 20° C., the mixture was poured into 150 cm³ of ice-cold water. The medium was extracted 3 times with 150 cm³ of dichloromethane. The organic extracts were washed 3 times with 100 cm³ of water and dried over sodium sulphate. After filtration and concentration under reduced pressure (5.2 kPa), the compound obtained was purified by chromatography on silica gel (0.06–0.20 mm). Elution was carried out with 7.8 liters of a dichloromethane-ethanol mixture (97-3 by volume), and 200 cm³ fractions were collected. The fractions between 5.6 and 7.8 liters were concentrated under reduced pressure (5.2 kPa). 0.77 g of ethyl 9-fluoro-8-[4-(4-fluorophenyl)piperazin-1-yl]-4-methyl-1-oxo-1,4-dihydrobenzo[f][1,7]naphthyridine-2-carboxylate was obtained in the form of yellow crystals, which melted at 300° C.

Ethyl 8,9-difluoro-4-methyl-1-oxo-1,4-dihydrobenzo[f][1,7]naphthyridine-2-carboxylate was prepared according to the method described in Example 2.

EXAMPLE 16

9-Fluoro-4-methyl-1-oxo-8-pyrrolidinyl-1,4-dihydrobenzo[f][1,7]naphthyridine-2-carboxylic Acid was Prepared in the Following Manner:

A suspension of 0.8 g of ethyl 9-fluoro-4-methyl-1-oxo-8-pyrrolidinyl-1,4-dihydrobenzo[f][1,7]naphthyridine-2-carboxylate in a mixture of 60 Cm³ of aqueous ethanol at 50% and 2.8 cm³ of a 1 N aqueous potassium hydroxide solution was heated, with stirring, for 2 hours at a temperature of 70° C. After concentration under reduced pressure (5.2 kPa) at 60° C., the residue was dissolved in 100 cm³ of water; the light insoluble material was removed by filtration. The solution obtained was neutralized with 2.8 cm³ of a 1 N aqueous hydrochloric acid solution. The insoluble material formed was dewatered, washed 3 times with 20 cm of water, twice with 15 cm³ of ethanol and dried under vacuum at 100° C. 0.65 g of 9-fluoro-4-methyl-1-oxo-8-pyrrolidinyl-1,4-dihydrobenzo[f][1,7]naphthyridine-2-carboxylic acid was obtained in the form of yellow crystals, which melted at 365° C.

Ethyl 9-fluoro-4-methyl-1-oxo-8-pyrrolidinyl-1,4-dihydrobenzo[f][1,7]naphthyridine-2-carboxylate was Prepared in the Following Manner:

A suspension of 2 g of ethyl 8,9-difluoro-4-methyl-1-oxo-1,4-dihydrobenzo[f][1,7]naphthyridine-2-carboxylate and 1.1 g of pyrrolidine in 40 cm³ of dimethylformamide was heated, with stirring, at a temperature of 70° C. for 8 hours. After cooling to 20° C., the mixture was poured into 150 cm³ of ice-cold water. The insoluble material was dewatered, washed 3 times with 30 cm³ of water, and dissolved in 300 cm³ of dichloromethane; the residual water was decanted off. The organic extracts were dried over sodium sulphate; after filtration and concentration under reduced pressure (5.2 kPa), the compound obtained was purified by chromatography on 180 g of silica gel (0.06–0.20 mm). Elution was carried out with 3.6 liters of a dichloromethane-ethanol mixture (97-3 by volume) and with 6 liters of a dichloromethane-ethanol mixture (94-6 by volume), 150 cm³ fractions were collected. The fractions obtained from the latter mixture were concentrated to dryness under reduced pressure. 0.85 g of ethyl 9-fluoro-4-methyl-1-oxo-8-pyrrolidinyl-1,4-dihydrobenzo[f][1,7]naphthyridine-2-carboxylate was obtained in the form of a yellow compound, which melted at 270° C.

Ethyl 8,9-difluoro-4-methyl-1-oxo-1,4-dihydrobenzo[f][1,7]naphthyridine-2-carboxylate was prepared according to the method described in Example 2.

EXAMPLE 17

For example, in a manner similar to the methods disclosed in the examples above, the following derivatives can also be prepared:

8-chloro-7-fluoro-9-[4-(3-fluoro-4-methylphenyl)piperazin-1-yl]-4-ethyl-1-oxo-1,4-dihydrobenzo[f][1,7]naphthyridine-2-carboxylic acid, 8-fluoro-4-methyl-1-oxo-9-[4-(3-fluoro-4-methylphenyl)piperazin-1-yl]-1,4-dihydrobenzo[f][1,7]naphthyridine-2-carboxylic acid, 8-fluoro-4-ethyl-1-oxo-9-[4-(3-fluoro-4-methylphenyl)piperazin-1-yl]-1,4-dihydrobenzo[f][1,7]naphthyridine-2-carboxylic acid, 8-fluoro-4-methyl-1-oxo-7-[4-(3-fluoro-4-methylphenyl)piperazin-1-yl]-1,4-dihydrobenzo[f][1,7]naphthyridine-2-carboxylic acid, 8-fluoro-4-ethyl-1-oxo-7-[4-(3-fluoro-4-methylphenyl)piperazin-1-yl]-1,4-dihydrobenzo[f][1,7]naphthyridine-2-carboxylic acid, 8-[4-(3-fluoro-4-methylphenyl)piperazin-1-yl]-9-fluoro-4-methyl-1-oxo-1,4-dihydrobenzo[f][1,7]naphthyridine-2-carboxylic acid, 8-[4-(3-fluoro-4-methyl phenyl)piperazin-1-yl]-9-fluoro-4-ethyl-1-oxo-1,4-dihydrobenzo[f][1,7]naphthyridine-2-carboxylic acid, 7-fluoro-8-[4-(3-fluoro-4-methylphenyl)piperazin-1-yl]-4-methyl-1-oxo-1,4-dihydrobenzo[f][1,7]naphthyridine-2-carboxylic acid, 7-fluoro-8-[4-(3-fluoro-4-methylphenyl)piperazin-1-yl]-4-ethyl-1-oxo-1,4-dihydrobenzo[f][1,7]naphthyridine-2-carboxylic acid, 8-chloro-7-fluoro-9-(1,3,3-trimethyl-6-azabicyclo[3.2.1]oct-6-yl)-4-methyl-1-oxo-1,4-dihydrobenzo[f][1,7]naphthyridine-2-carboxylic acid, 8-chloro-7-fluoro-9-(1,3,3-trimethyl-6-azabicyclo[3.2.1]oct-6-yl)-4-ethyl-1-oxo-1,4-dihydrobenzo[f][1,7]naphthyridine-2-carboxylic acid, 8-fluoro-4-ethyl-1-oxo-9-(1,3,3-trimethyl-6-azabicyclo[3.2.1]oct-6-yl)-1,4-dihydrobenzo[f][1,7]naphthyridine-2-carboxylic acid, 8-fluoro-4-methyl-1-oxo-7-(1,3,3-trimethyl-6-azabicyclo[3.2.1]oct-6-yl)-1,4-dihydrobenzo[f][1,7]naphthyridine-2-carboxylic acid, 8-fluoro-4-ethyl-1-oxo-7-(1,3,3-trimethyl-6-azabicyclo[3.2.1]oct-6-yl)-1,4-dihydrobenzo[f][1,7]naphthyridine-2-carboxylic acid, 8-(1,3,3,3-trimethyl-6-azabicyclo[3.2.1]oct-6-yl)-9-fluoro-4-methyl-1-oxo-1,4-dihydrobenzo[f][1,7]naphthyridine-2-carboxylic acid, 8-(1,3,3-trimethyl-6-azabicyclo[3.2.1]oct-6-yl)-9-fluoro-4-ethyl-1-oxo-1,4-dihydrobenzo[f][1,7]naphthyridine-2-carboxylic acid, 7-fluoro-8-(1,3,3-trimethyl-6-azabicyclo[3.2.1]oct-6-yl)-4-methyl-1-oxo-1,4-dihydrobenzo[f][1,7]naphthyridine-2-carboxylic acid, 7-fluoro-8-(1,3,3-trimethyl-6-azabicyclo[3.2.1]oct-6-yl)-4-ethyl-1-oxo-1,4-dihydrobenzo[f][1,7]naphthyridine-2-carboxylic acid, 8-chloro-7-fluoro-9-[4-(3-chloro-4-fluorophenyl)piperazin-1-yl]-4-ethyl-1-oxo-1,4-dihydrobenzo[f][1,7]naphthyridine-2-carboxylic acid, 8-fluoro-4-methyl-1-oxo-9-[4-(3-chloro-4-fluorophenyl)piperazin-1-yl]-1,4-dihydrobenzo[f][1,7]naphthyridine-2-carboxylic acid, 8-fluoro-4-ethyl-1-oxo-9-[4-3-chloro-4-fluorophenyl)piperazin-1-yl]-1,4-dihydrobenzo[f][1,7]naphthyridine-2-carboxylic acid, 8-fluoro-4-methyl-1-oxo-7-[4-(3-chloro-4-fluorophenyl)piperazin-1-yl]-1,4-dihydrobenzo[f][1,7]naphthyridine-2-carboxylic acid, 8-fluoro-4-ethyl-1-oxo-7-[4-(3-chloro-4-fluorophenyl)piperazin-1-yl]-1,4-dihydrobenzo[f][1,7]naphthyridine-2-carboxylic acid, 8-[4-(3-chloro-4-fluorophenyl)piperazin-1-yl]-9-fluoro-4-methyl-1-oxo-1,4-dihydrobenzo[f][1,7]naphthyridine-2-carboxylic acid, 8-[4-(3-chloro-4-fluorophenyl)piperazin-1-yl]-9-fluoro-4-ethyl-1-oxo-1,4-dihydrobenzo[f][1,7]naphthyridine-2-carboxylic acid, 7-fluoro-8-[4-(3-chloro-4-fluorophenyl)piperazin-1-yl]-4-methyl-1-oxo-1,4-dihydrobenzo[f][1,7]naphthyridine-2-carboxylic acid, 7-fluoro-8-[4-(3-chloro-4-fluorophenyl)piperazin-1-yl]-4-ethyl-1-oxo-1,4-dihydrobenzo[f][1,7]naphthyridine-2-carboxylic acid, 8-chloro-7-fluoro-9-[4-(3-trifluoromethylphenyl)piperazin-1-yl]-4-methyl-1-oxo-1,4-dihydrobenzo[f][1,7]naphthyridine-2-carboxylic acid, 8-chloro-7-fluoro-9-[4-(3-trifluoromethylphenyl)piperazin-1-yl]-4-ethyl-1-oxo-1,4-dihydrobenzo[f][1,7]naphthyridine-2-carboxylic acid, 8-fluoro-4-methyl-1-oxo-9-[4-(3-trifluoromethylphenyl)piperazin-1-yl]-1,4-dihydrobenzo[f][1,7]naphthyridine-2-carboxylic acid, 8-fluoro-4-ethyl-1-oxo-9-[4-(3-trifluoromethyl phenyl)piperazin-1-yl]-1,4-dihydrobenzo[f][1,7]naphthyridine-2-carboxylic acid, 8-fluoro-4-ethyl-1-oxo-7-[4-(3-trifluoromethylphenyl)piperazin-1-yl]-1,4-dihydrobenzo[f][1,7]naphthyridine-2-carboxylic acid, 8-[4-(3-trifluoromethylphenyl)piperazin-1-yl]-9-fluoro-4-methyl-1-oxo-1,4-dihydrobenzo[f][1,7]naphthyridine-2-carboxylic acid, 8-[4-(3-trifluoromethylphenyl)piperazin-1-yl]-9-fluoro-4-ethyl-1-oxo-1,4-dihydrobenzo[f][1,7]naphthyridine-2-carboxylic acid, 7-fluoro-8-[4-(3-trifluoromethylphenyl)piperazin-1-yl]-4-methyl-1-oxo-1,4-dihydrobenzo[f][1,7]naphthyridine-2-carboxylic acid, 7-fluoro-8-[4-(3-trifluoromethylphenyl)piperazin-1-yl]-4-ethyl-1-oxo-1,4-dihydrobenzo[f][1,7]naphthyridine-2-carboxylic acid, 8-chloro-7-fluoro-9-[3,3-dimethylpiperidino]-4-methyl-1-oxo-1,4-dihydrobenzo[f][1,7]naphthyridine-2-carboxylic acid, 8-chloro-7-fluoro-9-[3,3-dimethylpiperidino]-4-ethyl-1-oxo-1,4-dihydrobenzo[f][1,7]naphthyridine-2-carboxylic acid, 8-fluoro-4-ethyl-1-oxo-9-[3,3-dimethylpiperidino]-1,4-dihydrobenzo[f][1,7]naphthyridine-2-carboxylic acid, 8-fluoro-4-methyl-1-oxo-7-[3,3-dimethylpiperidino]-1,4-dihydrobenzo[f][1,7]naphthyridine-2-carboxylic acid, 8-fluoro-4-ethyl-1-oxo-7-[3,3-dimethylpiperidino]-1,4-dihydrobenzo[f][1,7]naphthyridine-2-carboxylic acid, 8-[3,3-dimethylpiperidino]-9-fluoro-4-methyl-1-oxo-1,4-dihydrobenzo[f][1,7]naphthyridine-2-carboxylic acid, 8-[3,3-dimethylpiperidino]-9-fluoro-4-ethyl-1-oxo-1,4-dihydrobenzo[f][1,7]naphthyridine-2-carboxylic acid, 7-fluoro-8-[3,3-dimethylpiperidino]-4-methyl-1-oxo-1,4-dihydrobenzo[f][1,7]naphthyridine-2-carboxylic acid, 7-fluoro-8-[3,3-dimethylpiperidino]-4-ethyl-1-oxo-1,4-dihydrobenzo[f][1,7]naphthyridine-2-carboxylic acid, 8-chloro-7-fluoro-9-[4-hydroxy-4-(3-trifluoromethyl phenyl)piperidin-1-yl]-4-methyl-1-oxo-1,4-dihydrobenzo[f][1,7]naphthyridine-2-carboxylic acid, 8-chloro-7-fluoro-9-[4-hydroxy-4-(3-trifluoromethyl phenyl)piperidin-1-yl]-4-ethyl-1-oxo-1,4-dihydrobenzo[f][1,7]naphthyridine-2-carboxylic acid, 8-fluoro-4-methyl-1-oxo-9-[4-hydroxy-4-(3-trifluoromethylphenyl)piperidin-1-yl]-1,4-dihydrobenzo[f][1,7]naphthyridine-2-carboxylic acid, 8-fluoro-4-ethyl-1-oxo-9-[4-hydroxy-4-(3-trifluoromethylphenyl)piperidin-1-yl]-1,4-dihydrobenzo[f][1,7]naphthyridine-2-carboxylic acid, 8-fluoro-4-ethyl-1-oxo-7-[4-hydroxy-4-(3-trifluoromethylphenyl)piperidin-1-yl]-1,4-dihydrobenzo[f][1,7]naphthyridine-2-carboxylic acid, 8-[4-hydroxy-4-(3-trifluoromethylphenyl)piperidin-1-yl]-9-fluoro-4-methyl-1-oxo-1,4-dihydrobenzo[f][1,7]naphthyridine-2-carboxylic acid, 8-[4-hydroxy-4-(3-trifluoromethylphenyl)piperidin-1-yl]-9-fluoro-4-ethyl-1-oxo-1,4-dihydrobenzo[f][1,7]naphthyridine-2-carboxylic acid, 7-fluoro-8-[4-hydroxy-4-(3-trifluoromethylphenyl)piperidin-1-yl]-4-methyl-1-oxo-1,4-dihydrobenzo[f][1,7]naphthyridine-2-carboxylic acid, 7-fluoro-8-[4-hydroxy-4-(3-trifluoromethylphenyl)piperidin-1-yl]-4-ethyl-1-oxo-1,4-dihydrobenzo[f][1,7]naphthyridine-2-carboxylic acid, 8-chloro-7-fluoro-9-[2-anilinomethyl-(2S)-pyrrolidino]-4-methyl-1-oxo-1,4-dihydrobenzo[f][1,7]naphthyridine-2-carboxylic acid, 8-chloro-7-fluoro-9-[2-anilinomethyl-(2S)-pyrrolidino]-4-ethyl-1-oxo-1,4-dihydrobenzo[f][1,7]naphthyridine-2-carboxylic acid, 8-fluoro-4-ethyl-1-oxo-9-[2-anilinomethyl-(2S)-pyrrolidino]-1,4-dihydrobenzo[f][1,7]naphthyridine-2-carboxylic acid, 8-fluoro-4-methyl-1-oxo-7-[2-anilinomethyl-(2S)-pyrrolidino]-1,4-dihydrobenzo[f][1,7]naphthyridine-2-carboxylic acid, 8-fluoro-4-ethyl-1-oxo-7-[2-anilinomethyl-(2S)-pyrrolidino]-1,4-dihydrobenzo[f][1,7]naphthyridine-2-carboxylic acid, 8-[2-anilinomethyl-(2S)-pyrrolidino]-9-fluoro-4-methyl-1-oxo-1,4-dihydrobenzo[f][1,7]naphthyridine-2-carboxylic acid, 8-[2-anilinomethyl-(2S)-pyrrolidino]-9-fluoro-4-ethyl-1-oxo-1,4-dihydrobenzo[f][1,7]naphthyridine-2-carboxylic acid, 7-fluoro-8-[2-anilinomethyl-(2S)-pyrrolidino]-4-methyl-1-oxo-1,4-dihydrobenzo[f][1,7]naphthyridine-2-carboxylic acid, 7-fluoro-8-[2-anilinomethyl-(2S)-pyrrolidino]-4-ethyl-1-oxo-1,4-dihydrobenzo[f][1,7]naphthyridine-2-carboxylic acid, 8-chloro-7-fluoro-9-[3-(4-benzyloxy-3-methoxyphenyl)-piperazin-1-yl]-4-methyl-1-oxo-1,4-dihydrobenzo[f][1,7]naphthyridine-2-carboxylic acid, 8-chloro-7-fluoro-9-[3-(4-benzyloxy-3-methoxyphenyl)-piperazin-1-yl]-4-ethyl-1-oxo-1,4-dihydrobenzo[f][1,7]naphthyridine-2-carboxylic acid, 8-fluoro-4-ethyl-1-oxo-9-[3-(4-benzyloxy-3-methoxyphenyl)piperazin-1-yl]-1,4-dihydrobenzo[f][1,7]naphthyridine-2-carboxylic acid, 8-fluoro-4-methyl-1-oxo-7-[3-(4-benzyloxy-3-methoxyphenyl)piperazin-1-yl]-1,4-dihydrobenzo[f][1,7]naphthyridine-2-carboxylic acid, 8-fluoro-4-ethyl-1-oxo-7-[3-(4-benzyloxy-3-methoxyphenyl)piperazin-1-yl]-1,4-dihydrobenzo[f][1,7]naphthyridine-2-carboxylic acid, 8-[3-(4-benzyloxy-3-methoxyphenyl)piperazin-1-yl]-9-fluoro-4-methyl-1-oxo-1,4-dihydrobenzo[f][1,7]naphthyridine-2-carboxylic acid, 8-[3-(4-benzyloxy-3-methoxyphenyl)piperazin-1-yl]-9-fluoro-4-ethyl-1-oxo-1,4-dihydrobenzo[f][1,7]naphthyridine-2-carboxylic acid, 7-fluoro-8-[3-(4-benzyloxy-3-methoxyphenyl)piperazin-1-yl]-4-methyl-1-oxo-1,4-dihydrobenzo[f][1,7]naphthyridine-2-carboxylic acid, 7-fluoro-8-[3-(4-benzyloxy-3-methoxyphenyl)piperazin-1-yl]-4-ethyl-1-oxo-1,4-dihydrobenzo[f][1,7]naphthyridine-2-carboxylic acid, 8-chloro-7-fluoro-9-[4-(3-methoxyphenyl)-3-methylpiperazin-1-yl]-4-methyl-1-oxo-1,4-dihydrobenzo[f][1,7]naphthyridine-2-carboxylic acid, 8-chloro-7-fluoro-9-[4-(3-methoxyphenyl)-3-methylpiperazin-1-yl]-4-ethyl-1-oxo-1,4-dihydrobenzo[f][1,7]naphthyridine-2-carboxylic acid, 8-fluoro-4-ethyl-1-oxo-9-[4-(3-methoxyphenyl)-3-methyl piperazin-1-yl]-1,4-dihydrobenzo[f][1,7]naphthyridine-2-carboxylic acid, 8-fluoro-4-methyl-1-oxo-7-[4-(3-methoxyphenyl)-3-methylpiperazin-1-yl]-1,4-dihydrobenzo[f][1,7]naphthyridine-2-carboxylic acid, 8-fluoro-4-ethyl-1-oxo-7-[4-(3-methoxyphenyl)-3-methylpiperazin-1-yl]-1,4-dihydrobenzo[f][1,7]naphthyridine-2-carboxylic acid, 8-[4-(3-methoxyphenyl)-3-methylpiperazin-1-yl]-8-fluoro-4-methyl-1-oxo-1,4-dihydrobenzo[f][1,7]naphthyridine-2-carboxylic acid, 8-[4-(3-methoxyphenyl)-3-methylpiperazin-1-yl]-9-fluoro-4-ethyl-1-oxo-1,4-dihydrobenzo[f][1,7]naphthyridine-2-carboxylic acid, 7-fluoro-8-[4-(3-methoxyphenyl)-3-methylpiperazin-1-yl]-4-methyl-1-oxo-1,4-dihydrobenzo[f][1,7]naphthyridine-2-carboxylic acid, 7-fluoro-8-[4-(3-methoxyphenyl)-3-methylpiperazin-1-yl]-4-ethyl-1-oxo-1,4-dihydrobenzo[f][1,7]naphthyridine-2-carboxylic acid, 8-chloro-7-fluoro-9-[3-(3,4-dimethylphenyl)piperazin-1-yl]-4-methyl-1-oxo-1,4-dihydrobenzo[f][1,7]naphthyridine-2-carboxylic acid, 8-chloro-7-fluoro-9-[3-(3,4-dimethylphenyl)piperazin-1-yl]-4-ethyl-1-oxo-1,4-dihydrobenzo[f][1,7]naphthyridine-2-carboxylic acid, 8-fluoro-4-ethyl-1-oxo-9-[3-(3,4-dimethylphenyl)piperazin-1-yl]-1,4-dihydrobenzo[f][1,7]naphthyridine-2-carboxylic acid, 8-fluoro-4-methyl-1-oxo-7-[3-(3,4-dimethylphenyl)piperazin-1-yl]-1,4-dihydrobenzo[f][1,7]naphthyridine-2-carboxylic acid, 8-fluoro-4-ethyl-1-oxo-7-[3-(3,4-dimethylphenyl)piperazin-1-yl]-1,4-dihydrobenzo[f][1,7]naphthyridine-2-carboxylic acid, 8-[3-(3,4-dimethylphenyl)piperazin-1-yl]-9-fluoro-4-methyl-1-oxo-1,4-dihydrobenzo[f][1,7]naphthyridine-2-carboxylic acid, 8-[3-(3,4-dimethylphenyl)piperazin-1-yl]-9-fluoro-4-ethyl-1-oxo-1,4-dihydrobenzo[f][1,7]naphthyridine-2-carboxylic acid, 7-fluoro-8-[3-(3,4-dimethylphenyl)piperazin-1-yl]-4-methyl-1-oxo-1,4-dihydrobenzo[f][1,7]naphthyridine-2-carboxylic acid, 7-fluoro-8-[3-(3,4-dimethylphenyl)piperazin-1-yl]-4-ethyl-1-oxo-1,4-dihydrobenzo[f][1,7]naphthyridine-2-carboxylic acid, 8-chloro-7-fluoro-9-[4-(4-fluorophenyl)piperazin-1-yl]-4-methyl-1-oxo-1,4-dihydrobenzo[f][1,7]naphthyridine-2-carboxylic acid, 8-chloro-7-fluoro-9-[4-(4-fluorophenyl)piperazin-1-yl]-4-ethyl-1-oxo-1,4-dihydrobenzo[f][1,7]naphthyridine-2-carboxylic acid, 8-fluoro-4-methyl-1-oxo-9-[4-(4-fluorophenyl)piperazin-1-yl]-1,4-dihydrobenzo[f][1,7]naphthyridine-2-carboxylic acid, 8-fluoro-4-ethyl-1-oxo-9-[4-(4-fluorophenyl)piperazin-1-yl]-1,4-dihydrobenzo[f][1,7]naphthyridine-carboxylic acid, 8-fluoro-4-methyl-1-oxo-7-[4-(4-fluorophenyl)piperazin-1-yl]-1,4-dihydrobenzo[f][1,7]naphthyridine-2-carboxylic acid, 8-fluoro-4-ethyl-1-oxo-7-[4-(4-fluorophenyl)piperazin-1-yl]-1,4-dihydrobenzo[f][1,7]naphthyridine-2-carboxylic acid, 8-[4-(4-fluorophenyl)piperazin-1-yl]-9-fluoro-4-ethyl-1-oxo-1,4-dihydrobenzo[f][1,7]naphthyridine-2-carboxylic acid, 7-fluoro-8-[4-(4-fluorophenyl)piperazin-1-yl]-4-methyl-1-oxo-1,4-dihydrobenzo[f][1,7]naphthyridine-2-carboxylic acid, 7-fluoro-8-[4-(4-fluorophenyl)piperazin-1-yl]-4-ethyl-1-oxo-1,4-dihydrobenzo[f][1,7]naphthyridine-2-carboxylic acid, 8-chloro-7-fluoro-9-(pyrrolidinyl)-4-methyl-1-oxo-1,4-dihydrobenzo[f][1,7]naphthyridine-2-carboxylic acid, 8-chloro-7-fluoro-9-(pyrrolidinyl)-4-ethyl-1-oxo-1,4-dihydrobenzo[f][1,7]naphthyridine-2-carboxylic acid, 8-fluoro-4-methyl-1-oxo-9-(pyrrolidinyl)-1,4-dihydrobenzo[f][1,7]naphthyridine-2-carboxylic acid, 8-fluoro-4-ethyl-1-oxo-9-(pyrrolidinyl)-1,4-dihydrobenzo[f][1,7]naphthyridine-2-carboxylic acid, 8-fluoro-4-methyl-1-oxo-7-(pyrrolidinyl)-1,4-dihydrobenzo[f][1,7]naphthyridine-2-carboxylic acid, 8-fluoro-4-ethyl-1-oxo-7-(pyrrolidinyl)-1,4-dihydrobenzo[f][1,7]naphthyridine-2-carboxylic acid, 8-(pyrrolidinyl)-9-fluoro-4-ethyl-1-oxo-1,4-dihydrobenzo[f][1,7]naphthyridine-2-carboxylic acid, 7-fluoro-8-(pyrrolidinyl)-4-methyl-1-oxo-1,4-dihydrobenzo[f][1,7]naphthyridine-2-carboxylic acid, 7-fluoro-8-(pyrrolidinyl)-4-ethyl-1-oxo-1,4-dihydrobenzo[f][1,7] naphthyridine-2-carboxylic acid, 8-chloro-7-fluoro-9-(3,3-dimethylpyrrolidinyl)-4-methyl-1-oxo-1,4-dihydrobenzo[f][1,7]naphthyridine-2-carboxylic acid, 8-chloro-7-fluoro-9-(3,3-dimethylpyrrolidinyl)-4-ethyl-1-oxo-1,4-dihydrobenzo[f][1,7]naphthyridine-2-carboxylic acid, 8-fluoro-4-methyl-1-oxo-9-(3,3-dimethylpyrrolidinyl)-1,4-dihydrobenzo[f][1,7]naphthyridine-2-carboxylic acid, 8-fluoro-4-ethyl-1-oxo-9-(3,3-dimethylpyrrolidinyl)-1,4-dihydrobenzo[f][1,7]naphthyridine-2-carboxylic acid, 8-fluoro-4-methyl-1-oxo-7-(3,3-dimethylpyrrolidinyl)-1,4-dihydrobenzo[f][1,7]naphthyridine-2-carboxylic acid, 8-fluoro-4-ethyl-1-oxo-7-(3,3-dimethylpyrrolidinyl)-1,4-dihydrobenzo[f][1,7]naphthyridine-2-carboxylic acid, 8-(3,3-dimethyl pyrrolidinyl)-9-fluoro-4-methyl-1-oxo-1,4-dihydrobenzo[f][1,7]naphthyridine-2-carboxylic acid, 8-(3,3-dimethylpyrrolidinyl)-9-fluoro-4-ethyl-1-oxo-1,4-dihydrobenzo[f][1,7]naphthyridine-2-carboxylic acid, 7-fluoro-8-(3,3-dimethylpyrrolidinyl)-4-methyl-1-oxo-1,4-dihydrobenzo[f][1,7]naphthyridine-2-carboxylic acid, 7-fluoro-8-(3,3-dimethylpyrrolidinyl)-4-ethyl-1-oxo-1,4-dihydrobenzo[f][1,7]naphthyridine-2-===carboxylic acid, 8-chloro-7-fluoro-9-(3-hydroxypyrrolidinyl)-4-methyl-1-oxo-1,4-dihydrobenzo[f][1,7]naphthyridine-2-carboxylic acid, 8-chloro-7-fluoro-9-(3-hydroxypyrrolidinyl)-4-ethyl-1-oxo-1,4-dihydrobenzo[f][1,7]naphthyridine-2-carboxylic acid, 8-fluoro-4-methyl-1-oxo-9-(3-hydroxypyrrolidinyl)-1,4-dihydrobenzo[f][1,7]naphthyridine-2-carboxylic acid, 8-fluoro-4-ethyl-1-oxo-9-(3-hydroxypyrrolidinyl)-1,4-dihydrobenzo[f][1,7]naphthyridine-2-carboxylic acid, 8-fluoro-4-methyl-1-oxo-7-(3-hydroxypyrrolidinyl)-1,4-dihydrobenzo[f][1,7]naphthyridine-2-carboxylic acid, 8-fluoro-4-ethyl-1-oxo-7-(3-hydroxypyrrolidinyl)-1,4-dihydrobenzo[f][1,7]naphthyridine-2-carboxylic acid, 8-(3-hydroxypyrrolidinyl)-9-fluoro-4-methyl-1-oxo-1,4-dihydrobenzo[f][1,7]naphthyridine-2-carboxylic acid, 8-(3-hydroxypyrrolidinyl)-9-fluoro-4-ethyl-1-oxo-1,4-dihydrobenzo[f][1,7]naphthyridine-2-carboxylic acid, 7-fluoro-8-(3-hydroxypyrrolidinyl)-4-methyl-1-oxo-1,4-dihydrobenzo[f][1,7]naphthyridine-2-carboxylic acid, 7-fluoro-8-(3-hydroxypyrrolidinyl)-4-ethyl-1-oxo-1,4-dihydrobenzo[f][1,7]naphthyridine-2-carboxylic acid, 8-chloro-7-fluoro-9-(piperidinyl)-4-methyl-1-oxo-1,4-dihydrobenzo[f][1,7]naphthyridine-2-carboxylic acid, 8-chloro-7-fluoro-9-(piperidinyl)-4-ethyl-1-oxo-1,4-dihydrobenzo[f][1,7]naphthyridine-2-carboxylic acid, 8-fluoro-4-methyl-1-oxo-9-(piperidinyl)-1,4-dihydrobenzo[f][1,7]naphthyridine-2-carboxylic acid, 8-fluoro-4-ethyl-1-oxo-9-(piperidinyl)-1,4-dihydrobenzo[f][1,7]naphthyridine-2-carboxylic acid,
8-fluoro-4-methyl-1-oxo-7-(piperidinyl)-1,4-dihydrobenzo[f][1,7]naphthyridine-2-carboxylic acid,
8-fluoro-4-ethyl-1-oxo-7-(piperidinyl)-1,4-dihydrobenzo[f][1,7]naphthyridine-2-carboxylic acid,
8-(piperidinyl)-9-fluoro-4-methyl-1-oxo-1,4-dihydrobenzo[f][1,7]naphthyridine-2-carboxylic acid,
8-(piperidinyl)-9-fluoro-4-ethyl-1-oxo-1,4-dihydrobenzo[f][1,7]naphthyridine-2-carboxylic acid,
7-fluoro-8-(piperidinyl)-4-methyl-1-oxo-1,4-dihydrobenzo[f][1,7]naphthyridine-2-carboxylic acid,
7-fluoro-8-(piperidinyl)-4-ethyl-1-oxo-1,4-dihydrobenzo[f][1,7]naphthyridine-2-carboxylic acid,
8-chloro-7-fluoro-9-(3-hydroxypiperidinyl)-4-methyl-1-oxo-1,4-dihydrobenzo[f][1,7]naphthyridine-2-carboxylic acid,
8-chloro-7-fluoro-9-(3-hydroxypiperidinyl)-4-ethyl-1-oxo-1,4-dihydrobenzo[f][1,7]naphthyridine-2-carboxylic acid,
8-fluoro-4-methyl-1-oxo-9-(3-hydroxypiperidinyl)-1,4-dihydrobenzo[f][1,7]naphthyridine-2-carboxylic acid,
8-fluoro-4-ethyl-1-oxo-9-(3-hydroxypiperidinyl)-1,4-dihydrobenzo[f][1,7]naphthyridine-2-carboxylic acid,
8-fluoro-4-methyl-1-oxo-7-(3-hydroxypiperidinyl)-1,4-dihydrobenzo[f][1,7]naphthyridine-2-carboxylic acid,
8-fluoro-4-ethyl-1-oxo-7-(3-hydroxypiperidinyl)-1,4-dihydrobenzo[f][1,7]naphthyridine-2-carboxylic acid,
8-(3-hydroxypiperidinyl)-9-fluoro-4-methyl-1-oxo-1,4-dihydrobenzo[f][1,7]naphthyridine-2-carboxylic acid,
8-(3-hydroxypiperidinyl)-9-fluoro-4-ethyl-1-oxo-1,4-dihydrobenzo[f][1,7]naphthyridine-2-carboxylic acid,
7-fluoro-4-(3-hydroxypiperidinyl)-4-methyl-1-oxo-1,4-dihydrobenzo[f][1,7]naphthyridine-2-carboxylic acid,
7-fluoro-8-(3-hydroxypiperidinyl)-4-ethyl-1-oxo-1,4-dihydrobenzo[f][1,7]naphthyridine-2-carboxylic acid,
8-chloro-7-fluoro-9-(4,4-dimethylpiperidinyl)-4-methyl-1-oxo-1,4-dihydrobenzo[f][1,7]naphthyridine-2-carboxylic acid,
8-chloro-7-fluoro-9-(4,4-dimethylpiperidinyl)-4-ethyl-1-oxo-1,4-dihydrobenzo[f][1,7]naphthyridine-2-carboxylic acid,
8-fluoro-4-methyl-1-oxo-9-(4,4-dimethylpiperidinyl)-1,4-dihydrobenzo[f][1,7]naphthyridine-2-carboxylic acid,
8-fluoro-4-ethyl-1-oxo-9-(4,4-dimethylpiperidinyl)-1,4-dihydrobenzo[f][1,7]naphthyridine-2-carboxylic acid,
8-fluoro-4-methyl-1-oxo-7-(4,4-dimethylpiperidinyl)-1,4-dihydrobenzo[f][1,7]naphthyridine-2-carboxylic acid,
8-fluoro-4-ethyl-1-oxo-7-(4,4-dimethyl piperidinyl)-1,4-dihydrobenzo[f][1,7]naphthyridine-2-carboxylic acid,
8-(4,4-dimethylpiperidinyl)-9-fluoro-4-methyl-1-oxo-1,4-dihydrobenzo[f][1,7]naphthyridine-2-carboxylic acid,
8-(4,4-dimethylpiperidinyl)-9-fluoro-4-ethyl-1-oxo-1,4-dihydrobenzo[f][1,7]naphthyridine-2-carboxylic acid,
7-fluoro-8-(4,4-dimethylpiperidinyl)-4-methyl-1-oxo-1,4-dihydrobenzo[f][1,7]naphthyridine-2-carboxylic acid,
7-fluoro-8-(4,4-dimethylpiperidinyl)-4-ethyl-1-oxo-1,4-dihydrobenzo[f][1,7]naphthyridine-2-carboxylic acid,
8-chloro-7-fluoro-9-[4-(3,4-difluorophenyl)piperazin-1-yl]-4-methyl-1-oxo-1,4-dihydrobenzo[f][1,7]naphthyridine-2-carboxylic acid,
8-chloro-7-fluoro-9-[4-(3,4-difluorophenyl)piperazin-1-yl]-4-ethyl-1-oxo-1,4-dihydrobenzo[f][1,7]naphthyridine-2-carboxylic acid,
8-fluoro-4-methyl-1-oxo-9-[4-(3,4-difluorophenyl)piperazin-1-yl]-1,4-dihydrobenzo[f][1,7]naphthyridine-2-carboxylic acid,
8-fluoro-4-ethyl-1-oxo-9-[4-(3,4-difluorophenyl)piperazin-1-yl]-1,4-dihydrobenzo[f][1,7]naphthyridine-2-carboxylic acid,
8-fluoro-4-methyl-1-oxo-7-[4-(3,4-difluorophenyl)piperazin-1-yl]-1,4-dihydrobenzo[f][1,7]naphthyridine-2-carboxylic acid,
8-fluoro-4-ethyl-1-oxo-7-[4-(3,4-difluorophenyl)piperazin-1-yl]-1,4-dihydrobenzo[f][1,7]naphthyridine-2-carboxylic acid,
8-[4-(3,4-difluorophenyl)piperazin-1-yl]-9-fluoro-4-methyl-1-oxo-1,4-dihydrobenzo[f][1,7]naphthyridine-2-carboxylic acid,
8-[4-(3,4-difluorophenyl)piperazin-1-yl]-9-fluoro-4-ethyl-1-oxo-1,4-dihydrobenzo[f][1,7]naphthyridine-2-carboxylic acid,
7-fluoro-8-[4-(3,4-difluorophenyl)piperazin-1-yl]-4-methyl-1-oxo-1,4-dihydrobenzo[f][1,7]naphthyridine-2-carboxylic acid,
7-fluoro-8-[4-(3,4-difluorophenyl)piperazin-1-yl]-4-ethyl-1-oxo-1,4-dihydrobenzo[f][1,7]naphthyridine-2-carboxylic acid,
8-chloro-7-fluoro-9-[4-hydroxy-4-(4-fluorophenyl)piperidinyl]-4-methyl-1-oxo-1,4-dihydrobenzo[f][1,7]naphthyridine-2-carboxylic acid,
8-chloro-7-fluoro-9-[4-hydroxy-4-(4-fluorophenyl)piperidinyl]-4-ethyl-1-oxo-1,4-dihydrobenzo[f][1,7]naphthyridine-2-carboxylic acid,
8-fluoro-4-methyl-1-oxo-9-[4-hydroxy-4-(4-fluorophenyl)piperidinyl]-1,4-dihydrobenzo[f][1,7]naphthyridine-2-carboxylic acid,
8-fluoro-4-ethyl-1-oxo-9-[4-hydroxy-4-(4-fluorophenyl)piperidinyl]-1,4-dihydrobenzo[f][1,7]naphthyridine-2-carboxylic acid,
8-fluoro-4-methyl-1-oxo-7-[4-hydroxy-4-(4-fluorophenyl)piperidinyl]-1,4-dihydrobenzo[f][1,7]naphthyridine-2-carboxylic acid,
8-fluoro-4-ethyl-1-oxo-7-[4-hydroxy-4-(4-fluorophenyl)piperidinyl]-1,4-dihydrobenzo[f][1,7]naphthyridine-2-carboxylic acid,
8-[4-hydroxy-4-(4-fluorophenyl)piperidinyl]-9-fluoro-4-methyl-1-oxo-1,4-dihydrobenzo[f][1,7]naphthyridine-2-carboxylic acid,
8-[4-hydroxy-4-(4-fluorophenyl)piperidinyl]-9-fluoro-4-ethyl-1-oxo-1,4-dihydrobenzo[f][1,7]naphthyridine-2-carboxylic acid,
7-fluoro-8-[4-hydroxy-4-(4-fluorophenyl)piperidinyl]-4-methyl-1-oxo-1,4-dihydrobenzo[f][1,7]naphthyridine-2-carboxylic acid,
7-fluoro-8-[4-hydroxy-4-(4-fluorophenyl)piperidinyl]-4-ethyl-1-oxo-1,4-dihydrobenzo[f][1,7]naphthyridine-2-carboxylic acid,
8-chloro-7-fluoro-9-(4-hydroxy-4-methylpiperidinyl)-4-methyl-1-oxo-1,4-dihydrobenzo[f][1,7]naphthyridine-2-carboxylic acid,
8-chloro-7-fluoro-9-(4-hydroxy-4-methylpiperidinyl)-4-ethyl-1-oxo-1,4-dihydrobenzo[f][1,7]naphthyridine-2-carboxylic acid,
8-fluoro-4-methyl-1-oxo-9-(4-hydroxy-4-methylpiperidinyl)-1,4-dihydrobenzo[f][1,7]naphthyridine-2-carboxylic acid,
8-fluoro-4-ethyl-1-oxo-9-(4-hydroxy-4-methylpiperidinyl)-1,4-dihydrobenzo[f][1,7]naphthyridine-2-carboxylic acid,
8-fluoro-4-methyl-1-oxo-7-(4-hydroxy-4-methylpiperidinyl)-1,4-dihydrobenzo[f][1,7]naphthyridine-2-carboxylic acid,
8-fluoro-4-ethyl-1-oxo-7-(4-hydroxy-4-methylpiperidinyl)-1,4-dihydrobenzo[f][1,7]naphthyridine-2-carboxylic acid, 8-(4-hydroxy-4-methyl piperidinyl)-9-fluoro-4-methyl-1-oxo-1,4-dihydrobenzo[f][1,7]naphthyridine-2-carboxylic acid, 8-(4-hydroxy-4-methylpiperidinyl)-9-fluoro-4-ethyl-1-oxo-1,4-dihydrobenzo[f][1,7]naphthyridine-2-carboxylic acid, 7-fluoro-8-(4-hydroxy-4-methylpiperidinyl)-4-methyl-1-oxo-1,4-dihydrobenzo[f][1,7]naphthyridine-2-carboxylic acid, and 7-fluoro-8-(4-hydroxy-4-methylpiperidinyl)-4-ethyl-1-oxo-1,4-dihydrobenzo[f][1,7]naphthyridine-2-carboxylic acid.

The present invention also relates to pharmaceutical compositions which can be used in human or veterinary medicine comprising, as active compound, at least one compound of formula (I), salt thereof, stereoisomer therof, or mixture of stereoisomers thereof, alone or in combination with at least one compatible and pharmaceutically acceptable diluent or adjuvant. These compositions may be used, for example, by the topical route.

The compositions for topical administration may be, for example, creams, ointments, gels, lotions, liniments or aerosols. They may also be pulverulent solid compositions.

When the compositions are creams, ointments or gels, these compositions may be, for example, hydrophilic ointments comprising, for example, a polyethylene glycol and appropriate quantities of water, hydrophobic ointments comprising, for example, petroleum jelly, paraffin, liquid paraffin, vegetable oils or animal fats, synthetic glycerides, waxes or liquid polyalkylsiloxanes. They may also be hydrophilic creams comprising, for example, oil-in-water emulsifying agents such as, for example, sodium or triethanolamine soaps, fatty alcohols, sulphated fatty alcohols, or polysorbates optionally in combination with water-in-oil emulsifying agents, or hydrophobic creams comprising, for example, water-in-oil emulsifying agents such as wool fat, sorbitan esters or monoglycerides. They may also be hydrophilic gels based on gelled propylene glycol, glycerol, alcohol or water, or hydrophobic gels comprising liquid paraffin supplemented with polyethylene, or fatty oils gelled with colloidal silicon oxide or aluminium or zinc soaps.

By way of example, when the compositions are aerosols, for use in the form of liquid aerosols, the compositions may be stable sterile solutions or solid compositions dissolved, at the time of use, in pyrogen-free sterile water, in saline or any other pharmaceutically acceptable vehicle. For use in the form of dry aerosols intended to be directly inhaled, the active ingredient is finely divided and combined with a water-soluble solid diluent or vehicle having a particle size of, for example, from 30 to 80 μm, for example dextran, mannitol or lactose.

In human or veterinary therapy, the compositions according to the invention are useful in the prophylactic or curative treatment of cutaneomucosal infections of Gram-positive bacterial origin, for example, the curative treatment of skin diseases caused by Gram-positive bacteria and/or the preventive treatment of infections caused by multiresistant Gram-positive bacteria, for example, in the treatment of infections associated with wounds, grafts or burns, in the treatment of infections related to skin lesions, or in the treatment of impetigos and furunculoses, as well as additionally for the prevention of the contamination of the nasal tracts by multiresistant Gram-positive bacteria, and also for decontamination so as to avoid the dissemination of these microorganisms.

In general, the doctor will determine the dosage which (s)he considers to be the most appropriate according to the age, the degree of the infection and other factors specific to the subject to be treated. The active ingredient can generally be present in an amount ranging from 1 to 2% in the formulation. Such a formulation can be applied, for example, 2 to 3 times per day by the topical route.

The following example, given with no limitation being implied, illustrates a composition according to the invention.

Example of Composition:

A cream containing a dose of 2% of free acid was prepared according to well-known, art-recognized techniques, which cream had the following composition:

| | |
|---|---|
| 8-chloro-7-fluoro-9-[4-(3-fluoro-4-methylphenyl)piperazin-1-yl]-4-methyl-1-oxo-1,4-dihydrobenzo[f][1,7]naphthyridine-2-carboxylic acid | 2.52 mg |
| cetomacrogol | 30.0 mg |
| benzyl alcohol | 3.0 mg |
| water for injection | 100 mg |

Moreover, compounds of formula (I) may also be used as agents for preserving or disinfecting organic or inorganic substances, for example, in the dye, fat, paper, wood or polymer industry or in the textile industry, the food industry or the treatment of water. It is also understood that compositions comprising at least one compound of formula (I), salt thereof, stereoisomer therof, or mixture of stereoisomers thereof, alone or in combination with at least one compatible diluent or adjuvant also fall within the scope of the present invention.

What is claimed is:

1. A benzo[f]naphthyridine compound chosen from benzo[f]naphthyridine compounds of formula (I), stereoisomers thereof, mixtures of stereoisomers thereof, metal salts thereof, nitrogenous base addition salts thereof, and acid addition salts thereof:

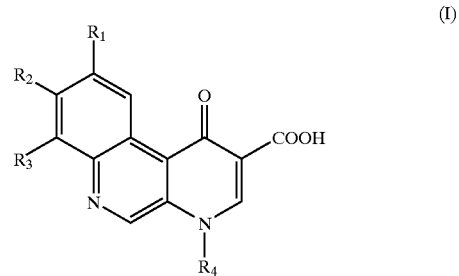

(I)

wherein $R_1$, $R_2$, and $R_3$, which are identical or different, are chosen from a hydrogen atom, halogen atoms, and groups of formula (II):

(II)

wherein:

$R_5$ and $R_6$ form, together with the nitrogen atom to which they are attached, a 5-, 6-, or 7-membered heterocycle, wherein 2 carbon atoms are optionally linked to each other by a bridge containing 1 or 2 carbon atoms, wherein said heterocycle optionally contains, in addition to said nitrogen atom, a heteroatom chosen from nitrogen, oxygen, and sulphur, and wherein said heterocycle is optionally substituted with at least one group chosen from (i) an unsubstituted phenyl group, (ii) a phenyl group substituted with at least one group chosen from halogen atoms, alkyl groups, haloalkyl groups, allyloxy groups, and a benzyloxy group, (iii) a benzyl groups (iv) alkyl groups, (v) a hydroxyl group, (vi) aminoalkyl groups, (vii) alkylaminoalkyl groups, (viii) dialkylaminoalkyl groups, and (ix) benzylaminoalkyl groups, provided that at least one of said $R_1$, $R_2$, and $R_3$ is a group of formula (II), and provided that at least one of said $R_1$, $R_2$, and $R_3$ is chosen from halogen atoms, and $R_4$ is chosen from alkyl groups, fluoroalkyl groups, carboxyalkyl groups, ($C_3$ to $C_5$) cycloalkyl groups, a fluorophenyl group, a difluorophenyl group, alkyloxy groups, and alkylamino groups, wherein each of the foregoing alkyl groups are chosen from unbranched ($C_1$ to $C_4$) alkyl groups and branched ($C_1$ to $C_4$) alkyl groups.

2. A benzo[f]naphthyridine compound of formula (I) according to claim 1:

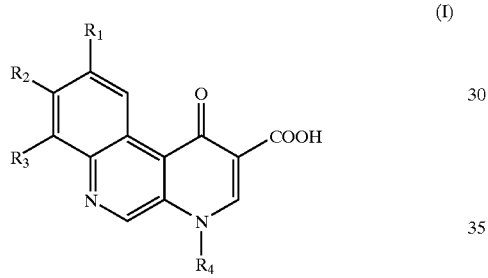

(I)

wherein:

$R_1$, $R_2$, and $R_3$, which are identical or different, are each chosen from a hydrogen atom, halogen atoms, and groups of formula (II):

(II)

wherein:

$R_5$ and $R_6$ form, together with the nitrogen atom to which they are attached, a 6- or 7-membered heterocycle, wherein 2 carbon atoms are optionally linked to each other by a bridge containing 1 or 2 carbon atoms, wherein said heterocycle optionally contains an additional nitrogen atom, and wherein said heterocycle is optionally substituted with at least one group chosen from (i) an unsubstituted phenyl group, (ii) a phenyl group substituted with at least one group chosen from halogen atoms, alkyl groups, haloalkyl groups, alkyloxy groups, and a benzyloxy group, and (iii) alkyl groups, provided that at least one of said $R_1$, $R_2$, and $R_3$ is a group of formula (II), and provided that at least one of said $R_1$, $R_2$, and $R_3$ is chosen from halogen atoms, and $R_4$ is chosen from alkyl groups and fluoroalkyl groups, wherein each of the foregoing alkyl groups are chosen from unbranched ($C_1$ to $C_4$) alkyl groups and branched ($C_1$ to $C_4$) alkyl groups.

3. A process for preparing a benzo[f]naphthyridine compound of formula (I) according to claim 1, said process comprising:

a) reacting an amine of formula (III):

(III)

wherein:

$R_5$ arid $R_8$ form, together with the nitrogen atom to which they are attached, a 5-, 6-, or 7-membered heterocycle, wherein 2 carbon atoms are optionally linked to each other by a bridge containing 1 or 2 carbon atoms, wherein said heterocycle optionally contains, in addition to said nitrogen atom, a heteroatom chosen from nitrogen, oxygen, arid sulphur, and wherein said heterocycle is optionally substituted with at least one group chosen from an (i) unsubstituted phenyl group, (ii) a phenyl group Substituted with at least one group chosen from halogen atoms, alkyl groups, haloalkyl groups, alkyloxy groups, and a benzyloxy group, (Iii) a benzyl group, (iv) alkyl groups, (v) a hydroxyl group, (vi) aminoalkyl groups, (vii) alkylaminoalkyl groups, (viii) dialkylaminoalkyl groups, and (ix) benzylaminoalkyl groups, with a benzo[f]naphthyridine compound of formula (IV):

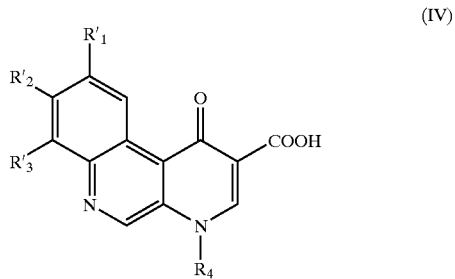

(IV)

wherein:

$R_4$ is chosen from alkyl groups, fluoroalkyl groups, carboxyalkyl groups, ($C_3$ to $C_6$) cycloalkyl groups, a fluorophenyl group, a difluorophenyl group, alkyloxy groups, alkylamino groups and protected alkylamino groups, and $R'_1$, $R'_2$, and $R'_3$, which are identical or different, are each chosen from a hydrogen atom and halogen atoms, provided that at least two of said $R'_1$, $R'_2$, and $R'_3$ are chosen from halogen atoms, wherein said halogen atoms are chosen from a fluorine atom, a chlorine atom, a bromine atom, and an iodine atom, b) optionally isolating a compound formed by said reaction, and c) optionally converting an isolated compound formed in b) to a salt.

4. A process for preparing a benzo[f]naphthyridine compound of formula (I) according to claim 1, said process comprising:

a) converting to an acid an ester of formula (V):

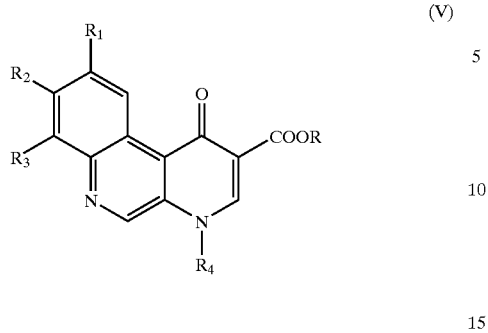

wherein:

R is chosen from unbranched ($C_1$ to $C_4$) alkyl groups and branched ($C_1$ to $C_4$) alkyl groups, $R_1$, $R_2$, and $R_3$, which are identical or different, are each chosen from a hydrogen atom, halogen atoms, and groups of formula (II):

wherein:

$R_5$ and $R_6$ form, together with the nitrogen atom to which they are attached, a 5-, 6-, or 7-membered heterocycle, wherein 2 carbon atoms are optionally linked to each other by a bridge containing 1 or 2 carbon atoms, wherein said heterocycle optionally contains, in addition to said nitrogen atom, a heteroatom chosen from nitrogen, oxygen, and sulphur, and wherein said heterocycle may be optionally substituted with at least one group chosen from an (i) unsubstituted phenyl group, (ii) a phenyl group substituted with at least one group chosen from halogen atoms, alkyl groups, haloalkyl groups, alkyloxy groups, and a benzyloxy group, (iii) a benzyl group, (iv) alkyl groups, (v) a hydroxyl group, (vi) aminoalkyl groups, (vii) alkylaminoalkyl groups, (viii) dialkylaminoalkyl groups, and (ix) benzylaminoalkyl groups, provided that at least one of $R_1$, $R_2$, and $R_3$ is a group of formula (II), and provided that at least one of $R_1$, $R_2$, and $R_3$ is chosen from halogen atoms, and $R_4$ is chosen from alkyl groups, fluoroalkyl groups, carboxyalkyl groups, ($C_3$ to $C_6$) cycloalkyl groups, a fluorophenyl group, a difluorophenyl group, alkyloxy groups, alkylamino groups and protected alkylamino groups, b) optionally removing said protecting group from said alkylamino group, and c) optionally converting a compound formed in b) to a salt.

5. The process according to claim 4, said process further comprising preparing said ester of formula (V) by:

a) reacting an amine of formula (III):

wherein:

$R_5$ and $R_6$ form, together with the nitrogen atom to which they are attached, a 5-, 6-, or 7-membered heterocycle, wherein 2 carbon atoms are optionally linked to each other by a bridge containing 1 or 2 carbon atoms, wherein said heterocycle optionally contains, in addition to said nitrogen atom, a heteroatom chosen from nitrogen, oxygen, and sulphur, and wherein said heterocycle is optionally substituted with at least one group chosen from an (i) unsubstituted phenyl group, (ii) a phenyl group substituted with at least one group chosen from halogen atoms, alkyl groups, haloalkyl groups, alkyloxy groups, and a benzyloxy group, (iii) a benzyl group, (iv) alkyl groups, (v) a hydroxyl group, (vi) aminoalkyl groups, (vii) alkylaminoalkyl groups, (viii) dialkylaminoalkyl groups, and (ix) benzylaminoalkyl groups, with a benzo[f]naphthyridine compound of formula (VI):

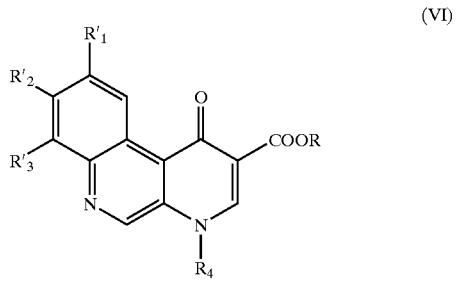

wherein:

$R'_1$, $R'_2$, and $R'_3$, which are identical or different, are each chosen from a hydrogen atom and halogen atoms, provided that at least two of said $R'_1$, $R'_2$, and $R'_3$ are chosen from halogen atoms, $R_4$ is chosen from alkyl groups, fluoroalkyl groups, carboxyalkyl groups, ($C_1$ to $C_6$) cycloalkyl groups, a fluorophenyl group, a difluorophenyl group, alkyloxy groups, alkylamino groups and protected alkylamino groups, and R is chosen from unbranched ($C_1$ to $C_4$) alkyl groups and branched ($C_1$ to $C_4$) alkyl groups, wherein said halogen atoms are Chosen from a fluorine atom, a chlorine atom, a bromine atom, and an iodine atom, b) optionally isolating said compound formed in a), and c) optionally converting said isolated compound formed in b) to a salt.

6. The process according to claim 5, said process further comprising preparing said compound of formula (VI) by:

a) reacting a malonate compound of formula (IX):

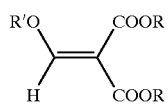

(IX)

wherein:

R and R', which are identical or different, are each chosen from unbranched ($C_1$ to $C_4$) alkyl groups and branched ($C_1$ to $C_4$) alkyl groups, with an aminoquinoline of formula (X):

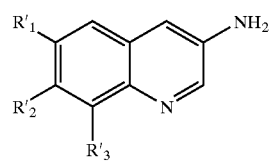

(X)

wherein:

$R'_1$, $R'_2$, and $R'_3$, which are identical or different, are each chosen from a hydrogen atom and halogen atoms, provided that at least two of said $R'_1$, $R'_2$, and $R'_3$ are chosen from halogen atoms, to form a compound of formula (VIII):

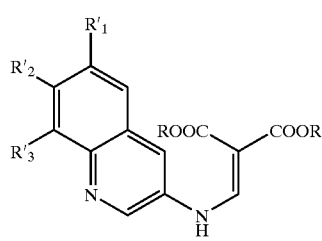

(VIII)

wherein:

$R'_1$, $R'_2$, and $R'_3$ are defined as above with respect to formula (X), and R is defined as above with respect for formula (IX), b) cyclizing said compound of formula (VIII) to form a compound of formula (VII):

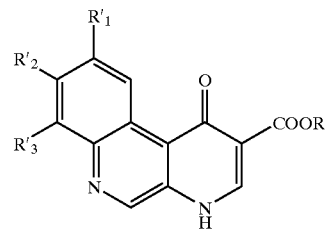

(VII)

wherein:

$R'_1$, $R'_2$, and $R'_3$ are defined as above with respect to formula (X), and R is defined as above with respect for formula (IX), c) reacting said compound of formula (VII) with a halogenated compound of formula $R_4$—Hal, wherein:

$R_4$ is chosen from alkyl groups, fluoroalkyl groups, carboxyalkyl groups, ($C_3$ to $C_6$) cycloalkyl groups, a fluorophenyl group, a difluorophenyl group, alkyloxy groups, alkylamino groups and protected alkylamino groups, and Hal is a halogen atom chosen from a chlorine atom, a bromine atom, and an iodine atom, b) optionally isolating said compound of formula (VIII) formed in a), and c) optionally converting said isolated compound formed in b) to a salt.

7. A composition comprising at least one benzo[f] naphthyridine compound of formula (I) according to claim 1.

8. A composition according to claim 7, further comprising at least one agent chosen from diluents and adjuvants.

9. A composition according to claim 8, wherein said diluents and adjuvants are chosen from pharmaceutically acceptable diluents and adjuvants.

10. A composition comprising at least one benzo[f] naphthyridine compound of formula (I) according to claim 2.

11. A composition according to claim 10, further comprising at least one agent chosen from diluents and adjuvants.

12. A composition according to claim 11, wherein said diluents and adjuvants are chosen from pharmaceutically acceptable diluents and adjuvants.

* * * * *

UNITED STATES PATENT AND TRADEMARK OFFICE
CERTIFICATE OF CORRECTION

PATENT NO.     : 6,566,362 B2
DATED          : May 20, 2003
INVENTOR(S)    : Jean-Francois Desconclois et al.

It is certified that error appears in the above-identified patent and that said Letters Patent is hereby corrected as shown below:

Column 42,
Line 51, "wherein" should read -- wherein: --.

Column 43,
Line 8, "allyloxy" should read -- alkyloxy --.
Line 9, "groups" should read -- group, --.

Column 44,
Line 17, "arid $R_8$" should read -- and $R_6$ --.
Line 23, "arid" should read -- and --.
Lines 26-27, "Substituted" should read -- substituted --.
Line 29, "(Iii)" should read -- (iii) --.

Column 46,
Line 51, "($C_1$ to $C_6$)" should read -- ($C_3$ to $C_6$) --.
Line 58, "Chosen" should read -- chosen --.

Signed and Sealed this

Fifteenth Day of July, 2003

JAMES E. ROGAN
*Director of the United States Patent and Trademark Office*